(12) United States Patent
Dunaway et al.

(10) Patent No.: US 10,861,587 B2
(45) Date of Patent: *Dec. 8, 2020

(54) CROSS-NETWORK GENOMIC DATA USER INTERFACE

(71) Applicant: Helix OpCo, LLC, San Mateo, CA (US)

(72) Inventors: Keith Dunaway, San Mateo, CA (US); Anna Merkoulovitch, San Francisco, CA (US); Andrew Shinohara, San Carlos, CA (US); Anupreet Walia, San Mateo, CA (US)

(73) Assignee: Helix OpCo, LLC, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/169,822

(22) Filed: Oct. 24, 2018

(65) Prior Publication Data

US 2020/0134136 A1 Apr. 30, 2020

(51) Int. Cl.
| | |
|---|---|
| *G06F 16/958* | (2019.01) |
| *G06F 16/9535* | (2019.01) |
| *G16B 45/00* | (2019.01) |
| *G16B 20/00* | (2019.01) |
| *G16B 50/00* | (2019.01) |

(52) U.S. Cl.
CPC ........... *G16B 45/00* (2019.02); *G06F 16/958* (2019.01); *G06F 16/9535* (2019.01); *G16B 20/00* (2019.02); *G16B 50/00* (2019.02)

(58) Field of Classification Search
USPC ........................................................ 709/217
See application file for complete search history.

(56) References Cited

U.S. PATENT DOCUMENTS

| | | | | |
|---|---|---|---|---|
| 7,873,024 B1* | 1/2011 | Fenwick | ............... | H04J 3/0673 370/350 |
| 9,367,800 B1* | 6/2016 | Do | ............... | G16B 45/00 |
| 9,594,598 B1* | 3/2017 | Brouwer | ............... | G06F 9/4856 |
| 2002/0169857 A1* | 11/2002 | Martija | ............... | H04L 29/06 709/220 |
| 2004/0107272 A1* | 6/2004 | Manukyan | ............... | G06F 9/44505 709/221 |
| 2005/0009031 A1* | 1/2005 | Becker | ............... | C12Q 1/6883 435/6.11 |
| 2006/0191995 A1* | 8/2006 | Stewart | ............... | G06Q 20/40 235/379 |

(Continued)

OTHER PUBLICATIONS

U.S. Appl. No. 16/146,864, filed Sep. 28, 2018, Genomic Network Service User Interface.

(Continued)

*Primary Examiner* — David R Lazaro
*Assistant Examiner* — Berhanu Shitayewoldetadik
(74) *Attorney, Agent, or Firm* — Schwegman Lundberg & Woessner, P.A.

(57) ABSTRACT

A genomic update system can generate a user interface from network pages based on variant data in one or more of the network pages matching user variant data. Some of the network pages may be in an elevated or trusted class and linking pages may link to those network pages. Content from the linking pages can be included with one or more visualizations in the user interface for interaction by a user via a user device, such as a handheld mobile device.

16 Claims, 27 Drawing Sheets

(56) References Cited

U.S. PATENT DOCUMENTS

| | | | | | |
|---|---|---|---|---|---|
| 2008/0095750 | A1* | 4/2008 | Gimble | ............... | A61K 35/28 424/93.7 |
| 2009/0077221 | A1* | 3/2009 | Eisenstadt | ............ | G06F 16/958 709/224 |
| 2010/0180029 | A1* | 7/2010 | Fourman | ................ | G06F 21/60 709/225 |
| 2010/0223281 | A1* | 9/2010 | Hon | .................. | G06F 16/2457 707/769 |
| 2010/0332404 | A1* | 12/2010 | Valin | ..................... | G06Q 99/00 705/310 |
| 2011/0072357 | A1* | 3/2011 | Arnstien | ............ | G06F 16/9577 715/738 |
| 2012/0092997 | A1* | 4/2012 | Mihaly | ................. | H04L 67/28 370/237 |
| 2013/0085681 | A1* | 4/2013 | Deciu | ................. | C12Q 1/6827 702/19 |
| 2013/0288244 | A1* | 10/2013 | Deciu | ................... | G16B 20/10 435/6.11 |
| 2014/0089009 | A1* | 3/2014 | Van Criekinge | ...... | G16H 10/60 705/3 |
| 2014/0115515 | A1* | 4/2014 | Adams | ................... | G16B 30/00 715/771 |
| 2014/0200166 | A1* | 7/2014 | Van Rooyen | ......... | G16B 30/00 506/38 |
| 2014/0371109 | A1* | 12/2014 | McMillen | ............ | H01L 23/528 506/38 |
| 2015/0248525 | A1* | 9/2015 | Ury | ....................... | G16H 10/60 705/3 |
| 2016/0015307 | A1* | 1/2016 | Kothuri | ................. | G16H 50/70 702/19 |
| 2017/0034654 | A1* | 2/2017 | Oberbeck | ........ | H04N 21/44213 |
| 2017/0068826 | A1* | 3/2017 | Dimitrova | ............. | G16B 50/00 |
| 2017/0078270 | A1* | 3/2017 | Tang | .................. | H04L 63/0815 |
| 2017/0124254 | A1* | 5/2017 | van Rooyen | ......... | H01L 27/118 |
| 2017/0193171 | A1* | 7/2017 | Perlroth | ................. | G16H 40/20 |
| 2017/0329915 | A1* | 11/2017 | Kittredge | ............... | G16B 45/00 |
| 2018/0374567 | A1* | 12/2018 | Toumazou | ......... | G06Q 30/0269 |
| 2019/0026428 | A1* | 1/2019 | Lu | .......................... | G16B 30/00 |
| 2019/0129737 | A1* | 5/2019 | Cheng | ................. | G06F 9/45533 |
| 2020/0104463 | A1* | 4/2020 | Glode | .................... | G16B 50/00 |
| 2020/0105365 | A1* | 4/2020 | Glode | .................... | G16B 40/00 |
| 2020/0134136 | A1* | 4/2020 | Dunaway | ............... | G16B 45/00 |
| 2020/0152310 | A1* | 5/2020 | Park | ....................... | G16H 20/30 |

OTHER PUBLICATIONS

U.S. Appl. No. 16/280,935, filed Feb. 20, 2019, Genomic Network Service User Interface.

"U.S. Appl. No. 16/280,935, First Action Interview—Pre-Interview Communication dated May 6, 2019", 4 pgs.

"U.S. Appl. No. 16/280,935, Response filed May 23, 2019 to First Action Interview—Pre-Interview Communication dated May 6, 2019", 2 pgs.

"U.S. Appl. No. 16/280,935, Examiner Interview Summary dated May 28, 2020", 3 pgs.

"U.S. Appl. No. 16/280,935, Final Office Action dated Feb. 6, 2020", 11 pgs.

"U.S. Appl. No. 16/280,935, First Action Interview—Office Action Summary dated Sep. 3, 2019", 10 pgs.

"U.S. Appl. No. 16/280,935, Response filed Jun. 8, 2020 to Final Office Action dated Feb. 6, 2020", 13 pgs.

"U.S. Appl. No. 16/280,935, Response filed Nov. 4, 2019 to First Action Interview—Office Action Summary dated Sep. 3, 2019", 26 pgs.

* cited by examiner

GENOME-WIDE ASSOCIATION STUDY

1600

| AUTHOR | SITE | IDENTIFIER | DESCRIPTION | |
|---|---|---|---|---|
| MORRIS, ET AL. | NATURE | RS3975778 | META-ANALYSIS FOLLOWED BY REPLICATION IDENTIFIES LOCI IN OR NEAR CD5 AND DRM5 AS ASSOCIATED WITH... | 1605 |
| EXAMPLE AUTHOR | EXAMPLE SITE | EXAMPLE IDENTIFIER | EXAMPLE DESCRIPTION | 1610 |
| EXAMPLE AUTHOR | EXAMPLE SITE | EXAMPLE IDENTIFIER | EXAMPLE DESCRIPTION | 1615 |
| ⋮ | | | | |
| EXAMPLE AUTHOR | EXAMPLE SITE | EXAMPLE IDENTIFIER | EXAMPLE DESCRIPTION | 1620 |

NATURE.COM

SYSTEMATIC ANALYSIS OF PHOTIC ALLERGIC REACTIONS IN POPULATIONS

MORRIS, ET AL. 2014

GENETIC POLYMORPHISMS ARE ASSOCIATED WITH PHOTIC ALLERGEIC REACTION ELEVATED RISK POTENTIAL. CLINICAL AND EPIDEMIOLOGICAL OBSERVATIONS SUGGEST THAT CLINICAL CHARACTERISTICS OF PHOTO SENSITIVE GENOTYPES, SUCH AS META-RECEPTOR 2 STATUS, ARE ALSO INFLUENCED BY HEREDITARY FACTORS. TO IDENTIFY A GENETIC VARIANT ASSOCIATED WITH PATHOLOGICAL CHARACTERISTICS OF PHOTIC SNEEZE PATIENTS, A STUDY WAS PERFORMED IN A GROUP OF 10,000 PATIENTS FROM ALL OVER THE WORLD VIA SIGNAL/PHARE STUDIES. REGARDING RS3975778, THE STRONGEST ASSOCIATION G/A POLYMORPHISM, 56.7% OF GG, 70.9% OF GA, AND 74.0% OF AA INDIVIDUALS REPORTED PHOTIC ALLERGETIC EFFECTS. THE 5F LOCUS IS KNOWN TO BE ASSOCIATED BASE AFFLICTIONS. OUR APPROACH PROVIDES SOUND EVIDENCE FOR AN ASSOCIATION BETWEEN VARIANTS IN THE F645R2 LOCUS AND ER STATUS AMONG PATIENTS, PARTICULARLY AMONG PATIENTS WITH....

*READ MORE!*

1705

ADDITIONAL LINKS:

SCIENCE NOW!
NEW WELSH TIMES
INDUSTRY BLOG

1710

FIG. 17

# CROSS-NETWORK GENOMIC DATA USER INTERFACE

FIELD

The present disclosure generally relates to special-purpose machines and improvements to such special-purpose machines, and to the technologies by which such special-purpose machines become improved compared to other special-purpose machines for generating a user interface comprising cross-network genomic data.

BACKGROUND

Users now have access to genomic tests and services that were recently available only through leading research organizations and clinical laboratories. The decreasing cost of genome sequencing has been one factor in increasing the availability of such direct-to-user genomic services. Such genomic services can now quickly complete laboratory analysis of a user's genome (e.g., deoxyribonucleic acid (DNA)), and give the user access to the newly generated genetic data (e.g., variant call format (VCF) file). These breakthrough advances have created several technological challenges due to the size, complexity, and nature of genetic data. For instance, while a given user can now have their genome sequenced, the resulting sequence data (e.g., sequence alignment/map (SAM) file) can often exceed hundreds of gigabytes of text data, which can be difficult to store and analyze even in a compressed format, let alone via mobile client device. Additionally, the sequenced data is very complex and understood by few users. Furthermore, access to the genetic data should be controlled in a secure way to ensure privacy of the user's genetic data.

BRIEF DESCRIPTION OF THE FIGURES

The inventive subject matter is more fully appreciated in connection with the following detailed description taken in conjunction with the accompanying drawings, in which:

FIG. 16 shows a database having one or more pages that originate from preselected servers, according to some example embodiments.

FIG. 17 shows an example root page, according to some example embodiments.

Like reference numerals refer to corresponding parts throughout the several views of the drawings.

DETAILED DESCRIPTION

Figure 1:
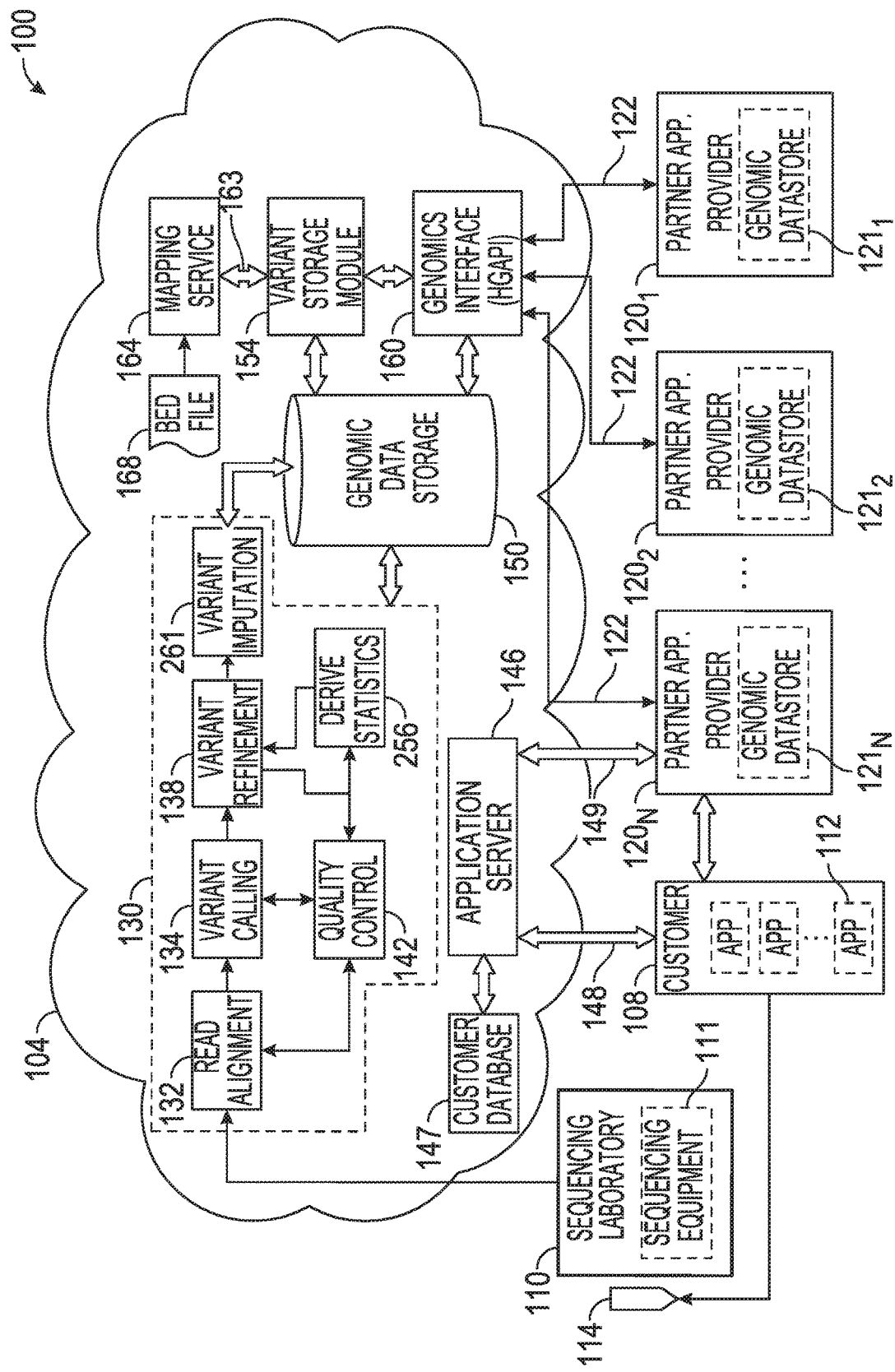
FIG. 1 illustrates a high-level architectural view of a system including a genomic services platform in accordance with the disclosure.

The description that follows discusses systems, methods, techniques, instruction sequences, and computing machine program products that illustrate examples of the present subject matter. For the purposes of explanation, numerous specific details are set forth in order to provide an understanding of various example embodiments of the present subject matter. It will be evident, however, to those skilled in the art, that example embodiments of the present subject matter may be practiced without these specific details.

As discussed, there are several difficulties in managing a user's genetic data. To this end, a genomic update system can generate a user interface that displays content structured from different network servers based on the user's genetic data. The content included in the user interface can depend on how the user's genetic data matches genetic data in a root page from a trusted network site. A trusted network site is a site trusted for accurate scientific data (e.g., a network site publishing peer reviewed articles). The root page may link to additional network pages on different sites, which can be included for display in the user interface. In some example embodiments, the user data can match the variant data in the root page in different ways (e.g., exact match, statistical match), as discussed in further detail below. In some example embodiments, a visualization (e.g., a chart, a graph, a table) that has been pre-associated with match type is included in the user interface for display to the user. For example, if an exact match occurs a first type of visualization (e.g., a checkbox) is included in the user interface; whereas if a statistical match occurs a second and different type of visualization is included in the user interface. The root page may be hosted or originate from a trusted class of network sites. Pages from the trusted class of network sites (e.g., www.nature.com) may hyperlink to secondary pages from other network sites (e.g., a webpage article on www-.wallstreetjournal.com that references the page on www.nature.com).

In some example embodiments, content from the secondary pages is automatically parsed and included in the user interface with the user's genetic data, and one or more visualizations. In some example embodiments, the secondary pages may be of an elevated class of network sites, that are trusted but less so than the trusted class. For example, the elevated class may only include webpage articles published on newspaper websites. In some example embodiments, additional classes are created based on pages of the additional classes linking to the root or secondary pages. In some of those example embodiments, based on the seriousness or categorical selections made from a user, page content from different classes is included in user interface. For example, if the genetic variation is in a "fun" category (i.e., not life threatening, such as eye color), and further if the user data matches the genetic variation data in the root page, then page content from secondary or tertiary class (e.g., an article from a blog) can be included in the user interface. In contrast, if the genetic variation is more serious (e.g., heart-health related) only page content from the secondary or root pages is included in the user interface, according to some example embodiments.

Attention is now directed to FIG. 1, which illustrates a system 100 including a genomic services platform 104 in accordance with the disclosure. As shown, the system 100 includes a sequencing laboratory 110 organized to receive biological samples 114 from users (e.g., blood, saliva). The sequencing laboratory 110 may include next-generation sequencing (NGS) equipment 111 operative to perform sequencing operations upon the biological samples 114 in order to determine genomic sequence information corresponding to the users. The resulting genomic sequence information may then be provided to the genomic services platform 104 for data processing, data storage, and data access. Such users may possess client devices 108 (e.g., smartphones or laptop computers) storing software applications 112 downloaded or otherwise obtained from servers operated and provided by partner application providers 120. In one example embodiment, the genomic services platform 104 is operated by an entity having contractual relationships with each of the partner application providers 120 and may provide such providers with selective access to sets of the user genomic information stored by the platform 104.

In the embodiment of FIG. 1, the genomic services platform 104 may be implemented using "cloud" computing capabilities. As is known, cloud computing may be characterized as a model for facilitating on-demand network access to a shared pool of configurable computing resources (e.g., networks, servers, storage, applications, and services) that can be rapidly provisioned and released with minimal management effort or service provider interaction. Cloud systems can automatically control resources expended by utilizing metering capabilities with respect to, for example, storage, processing, bandwidth, and active user accounts. Various cloud service models are possible, including cloud software as a service (SaaS), cloud platform as a service (PaaS), and cloud infrastructure as a service (IaaS).

In the embodiment of FIG. 1 the genomic services platform 104 may operate on "private" cloud infrastructure provided and managed by one or more third-party organizations. For example, in the embodiment of FIG. 1 the platform 104 includes a bioinformatics processing network 130 operative in a cloud environment managed by a first third-party organization, with the remainder of the platform 104 operating on infrastructure (e.g., another subnetwork having a different network address) provided by a second third-party organization. In one embodiment, the bioinformatics processing network 130 operates within the BaseSpace Sequence Hub provided by Illumina, and the remainder of the platform 104 operates through an Amazon® Web Service (AWS) Cloud. In other embodiments, some or all of the platform 104 may be implemented using other cloud environments such as, for example, a Microsoft® Azure cloud or another third-party cloud such as DNA Nexus. As shown, the bioinformatics processing network 130 may include a read alignment module 132, a variant calling module 134, a variant refinement module 138, a quality control module 142, and a variant imputation module 261.

In other embodiments, the genomic services platform 104 may be implemented by using on-premise servers and other infrastructure rather than by using cloud-based services. Alternatively, hybrid implementations of the genomic services platform 104 including a combination of on-premise and cloud-based infrastructure are also within the scope of the present disclosure.

Referring again to FIG. 1, the genomics services platform 104 includes an application server 146 that provides a portal through which users may complete a registration process for access to developer applications. In some examples, the application server 146 has access to a user (or customer) database 147. The user database 147 stores data relating to new and existing users and may be accessed by the application server 146 for user authorization and credentialing purposes, for example. In some examples, and depending on the services requested, there may be a hand-off of user data to facilitate the co-ordination of services between the platform 104 and other partner application providers 120 (e.g., app developers), other sequencing laboratories 110, or generally between entities within the system 100.

Through a series of API calls 148 to an API endpoint, e.g., Helix™ Application Program Interface (HAPI), a user's application can invoke certain tasks at the application server 146 to be performed by the application server 146 or in association with other entities within the genomic services platform 104. Typically, tasks using this API will relate to updating user data stored in the user database 147 and may include aspects such as querying data, adding or deleting data, and obtaining metadata about the data. Such applications offered through the portal established by the application server 146 may be the same as, or different from, the applications offered through the partner application providers 120.

Partner application providers 120 can also interact with the application server 146 in relation to non-genomic information. Through a series of API calls 149 to an API endpoint, e.g., Helix™ Partner Application Program Interface (HPAPI), a partner application provider 120 can also invoke certain tasks at the application server 146, such as querying user data, adding or deleting user data, and obtaining metadata about the user data.

Upon completing the registration process, in one embodiment a registered user is sent a receptacle (e.g., a tube or vial) into which the user may deposit a biological sample 114 (e.g., saliva). In one embodiment, the user may receive the receptacle via mail or a package delivery service and may send the receptacle containing the biological sample 114 to the sequencing laboratory 110 using the same or a similar mode of delivery. As part of the registration process, the user may be assigned a unique identifier (such as a unique "user registration ID", a "user ID", a "kitID", or another identifier described further below) that is imprinted or otherwise included on a label attached to the receptacle for the biological sample 114 sent to the user. The user ID may be in the form of a bar code for tracking progress of the user's biological sample through the sequencing laboratory 110 and in identifying the user's sample and related information in the bioinformatics processing network 130. The labeling associated with biological samples 114 sent to the sequencing laboratory 110 typically lacks any personal information enabling direct identification of the users associated with such samples 114.

In one embodiment, a user may register via the portal established by the application server 146 prior to ordering genomic-related applications or network services from partner application providers 120. In other embodiments, the user may access or download an application directly from a partner application provider 120 and provide registration or purchase information that is then forwarded to the platform 104 via an API endpoint, e.g., HPAPI. Upon receiving the registration information, the operator of the platform 104 may send a receptacle to the user for receiving a biological sample 114, which is subsequently sent by the user to the sequencing laboratory 110.

Figure 2:
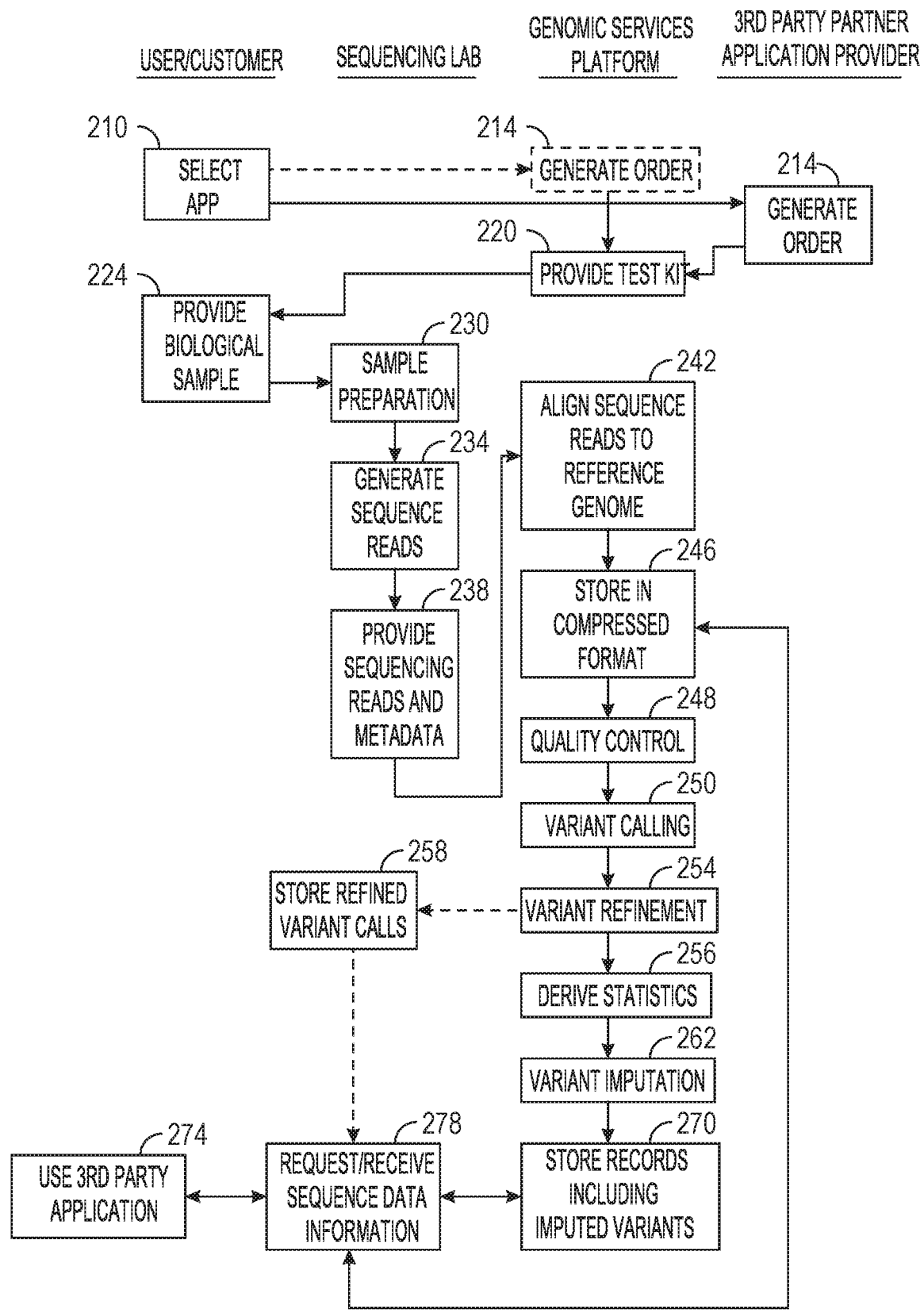
FIG. 2 illustrates an exemplary set of operations performed within the system of FIG. 1.

Attention is now directed to FIG. 2, which illustrates a flow diagram of operations performed within the system 100, according to some example embodiments. As shown, a user may select an application or network service through either the portal provided by the application server 146 or via a website or the like provided by a partner application provider 120 (stage 210). In response, either the application server 146 or the partner application provider 120 may generate an order (stage 214), which causes a test kit including a receptacle for a biological sample 114 to be sent to the user (stage 220). The user then provides the biological sample 114 to the sequencing laboratory 110 (stage 224).

Upon receiving the biological sample 114, the sequencing laboratory 110 prepares the sample 114 for sequencing (stage 230). As part of the preparation process, the sample 114 may be placed in a sample preparation cartridge to which reagents or other substances are added pursuant to the preparation protocol utilized. Such preparation of the sample 114 may include, for example, isolating or purifying the sample 114 and performing one or more of cleaving, degrading, annealing, hybridizing, denaturing, or ligating processes involving the sample 114. These processes may in some examples occur during transit of the sample 114 to the sequencing laboratory 110. Any suitable sample preparation operation known to those of ordinary skill in the art may be employed during stage 230.

Once the biological sample 114 has been prepared, it is processed by sequencing equipment 111 operative to generate observed genomic sequence reads and related quality score information (stage 234). The sequence reads generated may correspond to some or all of the user's genome sequence including, for example, genomic DNA, cDNA, hnRNA, mRNA, rRNA, tRNA, cRNA, and other forms of spliced or modified RNA. In exemplary embodiments, the sequence reads may relate to, for example, somatic, germline, gene expression, and transcriptome sequences.

Figure 3:
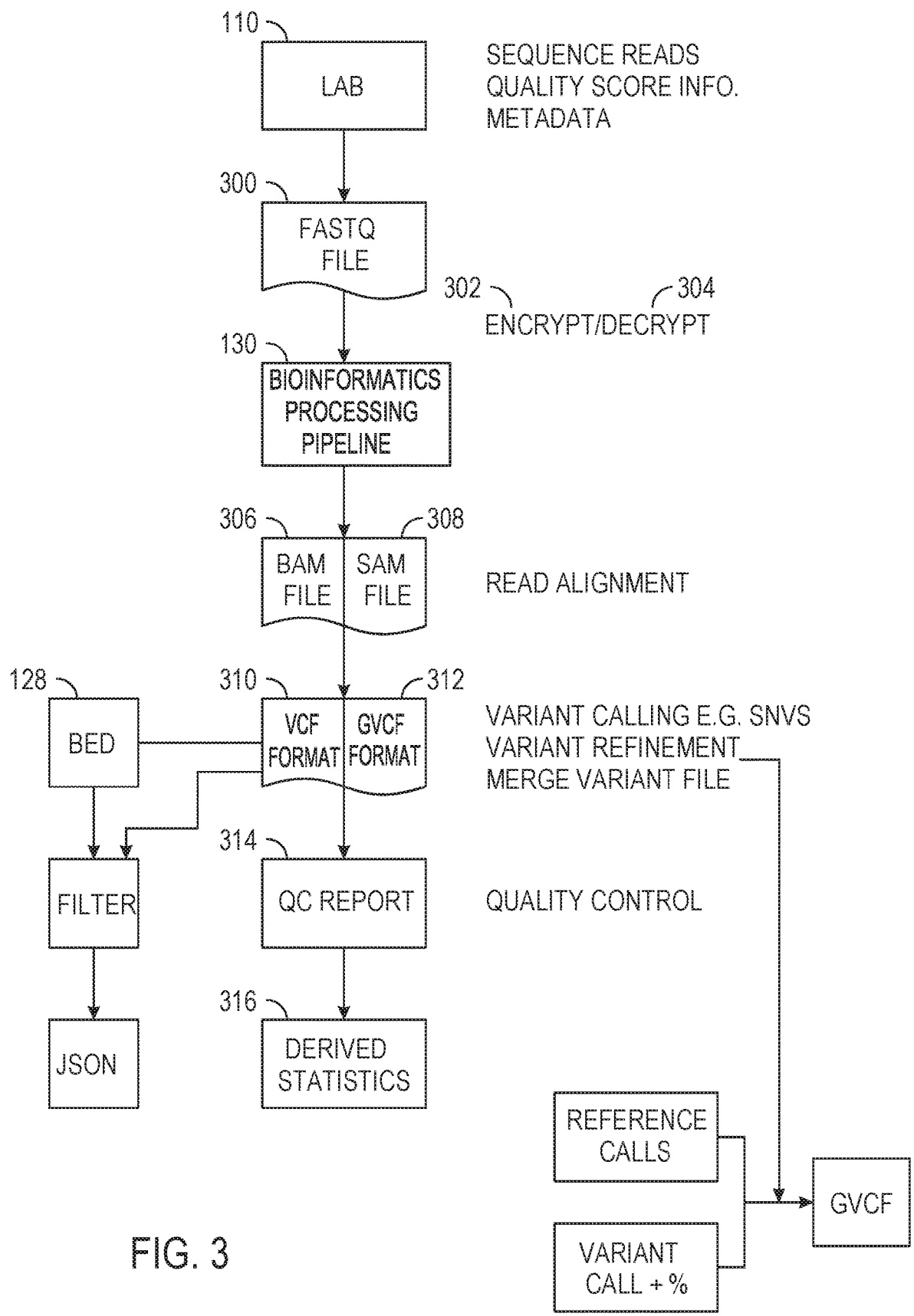
FIG. 3 illustrates an approach for processing sequenced data in different formats, according to some example embodiments.

With reference to FIG. 3, in one embodiment of the sequence reads, related quality score information and certain metadata generated by the sequencing laboratory 110 are included within a storage file 300 (such as a FASTQ file) which is electronically communicated to the bioinformatics processing network 130 (stage 238, FIG. 2). Generally, when sequencing is performed, raw image files are generated that can be used to identify which nucleotide is at a given read area. The FASTQ file format represents the raw read data from the generated images (e.g., 570 megabytes of raw read text data in 7.2 million rows, for a typical user). The FASTQ format can include the sequence string, consisting of the nucleotide sequence of each read, and can also include a quality score for every base. The storage file 300, or simply the raw images of sequence reads and related information, may be encrypted at 302 using one or more conventional techniques prior to being communicated to the bioinformatics processing network 130 and subsequently decrypted at 304. For example, the storage file 300 may be encrypted with a symmetric key, which may itself be encrypted. In some example embodiments, the storage file 300 can be encrypted and transferred using asymmetric key-pair.

As is discussed below, and with reference to FIG. 2 and FIG. 3, in one embodiment the bioinformatics processing network 130 uses this information from the sequencing laboratory 110 together with population variation data in order to perform the following operations:

1. Read Alignment: align the observed sequence reads in a FASTQ file to a reference genome, which may be in a non-FASTQ format (e.g., FASTA) and store the alignments in a file in a format such as a Sequence Alignment Map (SAM) file 308 (stage 242, FIG. 2), which, while compressed, can still exceed 1.4 GB with 1.4 million lines of text data. The SAM file 308 can be converted into a Binary Alignment Map (BAM) file 306 (e.g., a 7.5 GB text data file), which is a binary representation of the alignment data in the SAM file 308.

2. Variant Calling: compare the user's genome to the reference genome and identify variants such as a single nucleotide polymorphisms, insertions, and deletions and store these variants in a file format such as a variant call file 310 (VCF format), or genomic variant call file 312 (GVCF format) (stage 250, FIG. 2). The VCF format is a file format for storing DNA variation data such as single-nucleotide variants (SNVs), also called single-nucleotide polymorphisms (SNPs), and other variations, such as insertions/deletions (indels), structural variants, annotations, large structural variants, etc. Like FASTQ, SAM, and BAM files, a user's VCF file is often a very large file (e.g., hundreds of gigabytes of text data) having millions of rows, each row having multiple columns or fields of data. Each row of a VCF file corresponds to a variant at one genomic position or region. A VCF further has multiple columns or tab-delimited fields including, for example, a position column that specifies the start of the variant, a reference allele column of the reference genome, and a nonreference allele column comprising the user's allele value, for example.

3. Variant Refinement: perform additional processing and filtering to derive the final variant calls (stage 254, FIG. 2). In some examples, a ploidy correction is performed during the variant refinement step. Ploidy, in genetics, relates to the number of chromosomes occurring in the nucleus of a cell. A chromosome is a threadlike structure of nucleic acids and protein found in the nucleus of most living cells, carrying genetic information in the form of genes. In normal somatic (body) cells, chromosomes exist in pairs. The condition is called diploidy. During meiosis, the cell produces gametes, or germ cells, each containing half the normal or somatic number of chromosomes. This condition is called haploidy. When two germ cells (e.g., egg and sperm) unite, the diploid condition is restored. Polyploidy refers to cells the nuclei of which have three or more times the number of chromosomes found in haploid cells. Some cells have an abnormal number of chromosomes that is not typical for that organism. In some examples, a ploidy correction is performed by making a sex inference using a heuristic based on the ratio of high-quality reads mapped to chromosome Y divided by those mapped to chromosome X.

4. Quality Control: generate a quality control (QC) report 314 with QC metric values computed on the subject's read alignments and/or variant calls (stage 248, FIG. 2).

5. Derived Statistics: In one embodiment statistics 316 may be derived based upon, for example, sequence reads and/or variant information for use in quality control and process monitoring. In some alternate examples, a ploidy correction could be performed in this stage instead by making a sex inference using a heuristic based on the ratio of high-quality reads mapped to chromosome Y divided by those mapped to chromosome X (stage 256, FIG. 2). In some examples, derived statistics are obtained as part of the quality control stage, such that statistic derivation is not performed as a discrete, subsequent operation.

For each of the observed sequence reads in the FASTQ file, the read alignment module 132 determines a corresponding location in a reference sequence (or finds that no such location can be determined) (stage 242). The read alignment module 132 may utilize a mapping algorithm to compare the sequence of a given read to that of the reference sequence and attempt to locate a potentially unique location in the reference sequence that matches the read.

The results of the sequence alignment operation may be stored in a relatively compressed format such as, for example, in a compressed BAM file 306 (stage 246) or in a file utilizing another compressed storage format. The resulting BAM file 306 may, in one example, be indexed relative to the reference sequence (e.g., a SAM file 308) and analyzed by the quality control module 142 (stage 248). In one embodiment, the variant calling module 134 is configured to process the BAM file 308 in order to identify the existence of variants such as single nucleotide variants (SNVs) relative to the reference sequence (stage 250). The results of the variant calling process may be stored within, for example, one or more VCF files or in other variant call file formats. In one embodiment, the variant calling module 134 produces two variant data files, although in alternative implementations only a single variant data file may be produced. The first variant data file (e.g., GVCF 312) provides general information about all sites in the genome, which include both sites with and without variants (reference calls); the second variant data file (e.g., VCF 310) does not provide information for reference calls. The second variant data file (VCF) provides finalized posterior genotype likelihoods for variants (i.e., for each site at which a variant occurs, it gives the probability that the genotype it assigned to the sample at the site is incorrect). The first variant data file includes genotype likelihoods for variants, but they are not finalized as they may be based on incomplete or low-quality information or genotypes. The sequencing and alignment calling process can create many technical artifacts that can lead to inaccurate results. Using various quality metrics computed for the variants, quality filtering is performed on the second variant data file to remove such artifacts. After filtering, the second variant data file is merged with the first variant data file.

In one embodiment, variant refinement (stage 254) is performed with respect to variant and reference calls produced during stage 250 in order to generate a final variant call output of observed variants. As is discussed below, additional variant calls not directly determined by observed results of the sequencing process may be added during a subsequent variant imputation processing step. In some embodiments, for each sample 114 processed during stage 254, the variant refinement module 138 merges the two variant data files generated by the variant calling module 134 for the sample 114 into a single variant data file, merges records in the file that represent adjacent reference calls, merges records in the file that represent overlapping variant calls or reference calls, performs ploidy correction using derived statistics (stage 256), and performs variant filtering. By merging the two files produced by the variant calling module 134, the variant refinement module 138 produces a variant data file with reference calls from the first file and variants calls with posterior genotype likelihoods from the second file. In one embodiment, the variant data file will contain two types of records that can be merged: records representing adjacent reference calls and records representing overlapping variant calls or reference calls.

In some examples, the variant data file containing the refined variant calls produced by the variant refinement module 138 is stored within a genomic data storage 150 before variant imputation and may be encrypted using conventional techniques (stage 258). In one embodiment, the genomic data storage 150 is implemented using cloud-based storage such as, for example, Amazon Simple Storage Service (S3), which is available through Amazon Web Services™ (AWS). In general, S3 provides persistent storage for HTTP access to store and retrieve data.

In some examples, haplotype reference data is utilized in the variant imputation operation of stage 262 (FIG. 2). A reference haplotype can indicate what types of variants are found at given chromosome positions in a sequence. So, if a chromosome position is known, and a variant is detected at that position but the nature or type of the variant is not known (or is known but with a low degree of certainty or probability), reference to the known variants on the corresponding haplotype position can help to complete or "boost" (or impute) the missing information. These variant records including refined and imputed variants may then be encrypted using conventional techniques and stored within genomic data storage 150 (stage 270) for controlled access by a user or partner application provider 120 as described below.

In some example embodiments, when a user interacts with an application 112 obtained from a partner application provider 120, the application 112 may make requests to the partner application provider 120 which require the partner application provider 120 to access genomic information stored by the platform 104 (stage 274). Upon receiving such a request, the partner application provider 120 may issue a request for the relevant information through a genomics interface 160 of the platform 104 comprised of a network interface and a genomics API (stage 278). Referring again to FIG. 1, through a series of API calls 122 to an API endpoint, e.g., Helix™ Genomics Application Program Interface (HGAPI) at the genomics interface 160, a partner application can invoke certain tasks at the genomics interface 160 such as making requests, querying information, adding, updating or deleting information, and obtaining metadata (tags) about the information.

The various system APIs discussed herein (more specifically, the example API's described herein as HAPI, HPAPI, and HGAPI), allow a partner application provider 120 to integrate genetics into its applications, products, or services. The genomic services platform 104 supports multiple application providers. The APIs are designed to use consistent resource-oriented URLs as well as HTTP response codes to indicate errors. They also support built-in HTTP features, such as HTTP verbs, for compatibility with the majority of standard HTTP clients. All responses are returned as JSON messages.

Using the APIs, a partner can in some examples access two services based on development needs. Each service has both staging and production endpoints. The two hosted, dedicated services can be invoked to notify a partner application provider of user events and to give the partner access to the relevant genetic information that enables DNA-related features. The first service, for example accessible at the endpoint HPAPI, utilizes the user database 147 and can notify a partner about a user's status, including aspects such as where the user's biological sample 114 is in the sequencing process, if they have registered their DNA collection kit, and whether or not they have consented to share their genetic and personal information with the partner's application.

In some examples, the partner API (HPAPI) acts as an interface between the system 100 or platform 104 infrastructure and partner application provider 120 infrastructure. This service can provide certain non-genomic data a partner may need to enable their app to query genomic data and return results back to a user. In other aspects, the partner API service specifically notifies partners about one or more of the following events: a user has purchased an app and is granting permission for that app to access their genomic data, a user has submitted a saliva sample and that sample is being processed in the lab, a user's sample has completed sequencing and QC (Quality Control) and the genomic data is available to query, a user's genomic data has been updated due to an upgrade or a change in the bioinformatics processing network 130, a user has withdrawn consent and/or has funded or removed an app.

Some embodiments of a sample service within the system 100 store and serve sample statuses. With reference to the identifier definitions provided further above, an example sample service can perform, for example, the following functions: translation of inbound accessioning events from partner application providers 120 that contain a kitId and a user ID to a sampleId, translation of outbound (lab 110) sample status (e.g., BaseSpace sample status) with a sampleId to be identified with a kitId and a user ID, storage of sample statuses for retrieval, and publishing message queues to HPAPI or directly to partners on sample status updates.

In one example of an account update provided by the first service, a user can agree to share his or her relevant genomic and personal information with a partner application, verify an email address, and register a kit. The registration step can be important as a user purchasing a kit might not be the one submitting it. At the time of purchase, a kit will be sent in the mail and eventually a user will register that kit. Since the purchaser may be a different person than the sample provider, the user who delivers genetic data via the spit tube in a kit is not confirmed until that user registers the kit as their own.

The second service, for example accessible at the endpoint HGAPI, can be used to request the relevant genetic information that enables the partner's DNA-relevant features in its application. Accessing a user's variants (or markers), for example, is typically a primary use of this service. In some examples, a "no-call" is issued when the genomic services platform 104 is unable to make a call that met a minimum quality threshold due to lack of coverage or poor fit of the probabilistic variant calling model. A no-call is characterized by the presence of a specific entry, such as "−1", in the genotype array. In some examples, a "reference" call is issued when the genomic services platform 104 observes, in sufficient quantity and with sufficient quality, only bases matching the reference sequence. A reference call is characterized by the presence of only "0" entries in the genotype array. In some examples, a "variant" call is issued when the genomic services platform 104 observes, in sufficient quantity and with sufficient quality, bases not matching the reference sequence. A variant call is characterized by the presence of any element in the genotype array greater than 0, representing the presence of an alternative allele present in alternate bases. If the record is not a no-call or a reference call, then it is a variant call.

In some examples, an access token (e.g., OAuth access token) is needed any time a partner application calls a system API to read a user's information. When a partner requests an OAuth access token, it is required to define token parameters, such as grant type and scope. A partner will need credential pairs to continue, which can be generated by performing appropriate credentialing steps. All API requests are made over HTTPS. Calls made over plain HTTP will fail. API requests without authentication will also fail.

In some example embodiments, a request for relevant information from a partner application provider 120 includes a unique ID ("PAC ID" or user ID) that identifies a binary tuple of the form (app, user), where app is a value identifying one of the applications 112 for the partner application provider 120, and user is a value identifying the particular end-user interacting with the application 112 corresponding to the app. In some examples, the PAC ID may comprise a three-part tuple in the form of (partner, app, user) with corresponding values identifying a partner application provider 120, an application 112, and a user. Other combinations of values are possible, such as (partner, app). Irrespective of which PAC ID is used, an objective of a PAC ID is to allow a partner application provider 120 to refer to a user without knowing the actual "value" of the user and to maintain anonymity and privacy in health records. Upon receiving the request including the PAC ID ( ), the genomic interface 160 may present it to the variant storage module 154.

In one embodiment, the variant storage module 154 operates on a server-less framework in a cloud environment, such as Amazon Web Services (AWS Lambda). The AWS Lambda system allows the variant storage module 154 to run code without provisioning or managing servers. The variant storage module 154 accrues costs only for the compute time it consumes when running its functions. There is no charge when the code is not running. This can be important because call volume demands tend to be highly variable. In some examples, the variant storage module 154 receives in excess of one thousand requests per minute for information. The server-less arrangement is highly scalable and minimizes running costs for the variant storage module 154, and indirectly for partners and users. Using AWS Lambda, the variant storage module 154 can run code for virtually any type of partner or user application or backend service with very minimal or zero administration.

In some examples, the variant storage module 154 performs automated tests. The tests are run for any code change that must pass the tests before being deployed to production. For a given PAC ID, the variant storage module 154 may create and output a file and send to HGAPI an expected result that may be investigated if incorrect. In another example, a test (BED) file downloaded from the mapping service 164 is checked for conformity with an expected result. Other automated tests include checking that a request without a user ID (e.g., PAC ID) or app ID, or having a bad PAC ID or app ID, fails. Some data files used within the system 100 may be in a binary variant call format (BCF, or a BAM file described elsewhere herein), and each user may have an associated BCF. Given a BCF, further automated testing may check that filtering by a given region returns correct or expected test intervals, or does not contain a given interval. Other testing may check, again given a BCF file, that an open boundary condition is correctly handled, or that overlapping regions are correctly handled, or that compared to a converted VCF, certain results are expected. Other automated tests may include checking that a (BED) file can be opened correctly, or that if it cannot be opened correctly, an error message is thrown. Other testing may check for attempts to open non-existent (BED) files, or to check connectivity with the mapping service 164 such that given an invalid App ID and/or PAC ID, no (BED) file is returned. Other tests include reference block trimming, for example checking that a returned interval is always a subset of the applicable sequence region, or that a reference block that overlaps multiple regions returns correctly each restricted overlapping region. In some examples, the data used for automated tests is dummy data that mimics what real data will look like in production. In other examples, the test data is derived from real biological samples (cell lines) and modified to be used for testing.

Figure 4:
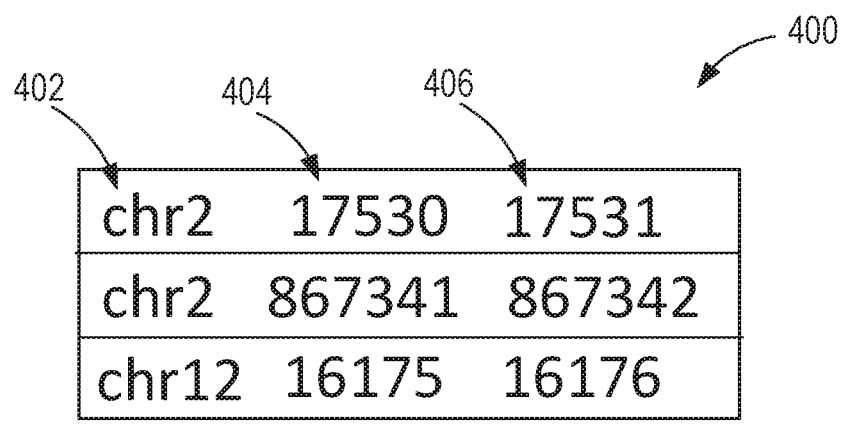
FIG. 4 displays an example Browser Extensible Data (BED) file that defines specific regions of a genome, according to some example embodiments.

FIG. 4 displays an example Browser Extensible Data (BED) file 400 that define specific regions of a genome. The file 400 includes three fields that define: a chromosome 402, a start position 404, and an end position 406 in the genome. Various conventions may be utilized to specify these locations. In some examples, a (BED) file 168 includes definitions of multiple "DNA windows" defining regions (e.g., one or more ranges of reference locations) of a user genome that may be requested by a particular partner application provider 120 or application 112 through the genomic interface 160.

For example, upon a request for user genomic data from a partner application provider 120 being received via genomic interface 160, the variant storage module 154 then retrieves all the variants pertaining to a user's genome and filters these based upon the PAC ID and the appropriate DNA window specified in the (BED) file 168. The fetched variants are then returned via a secure connection to the requesting partner application provider 120, and potentially stored by the requesting partner application provider 120 in an optional genomic datastore 121. This enables the partner application provider 120 to deliver corresponding variant data to the application 112 responsible for initiating the request for genomic information in a controlled and secure manner. The content of the corresponding variant data will generally be dependent upon the nature of the application 112. In this way, a user's genetic information can be sequenced once, stored indefinitely, and then queried again, potentially many times, to provide further biogenetic information in a secure manner.

Further details regarding selective access to genomic user data are found in Application Ser. No. 62/535,779, titled "Genomic Services Platform Supporting Multiple Application Providers", filed on Jul. 21, 2017, which is incorporated by reference in its entirety.

Figure 5:
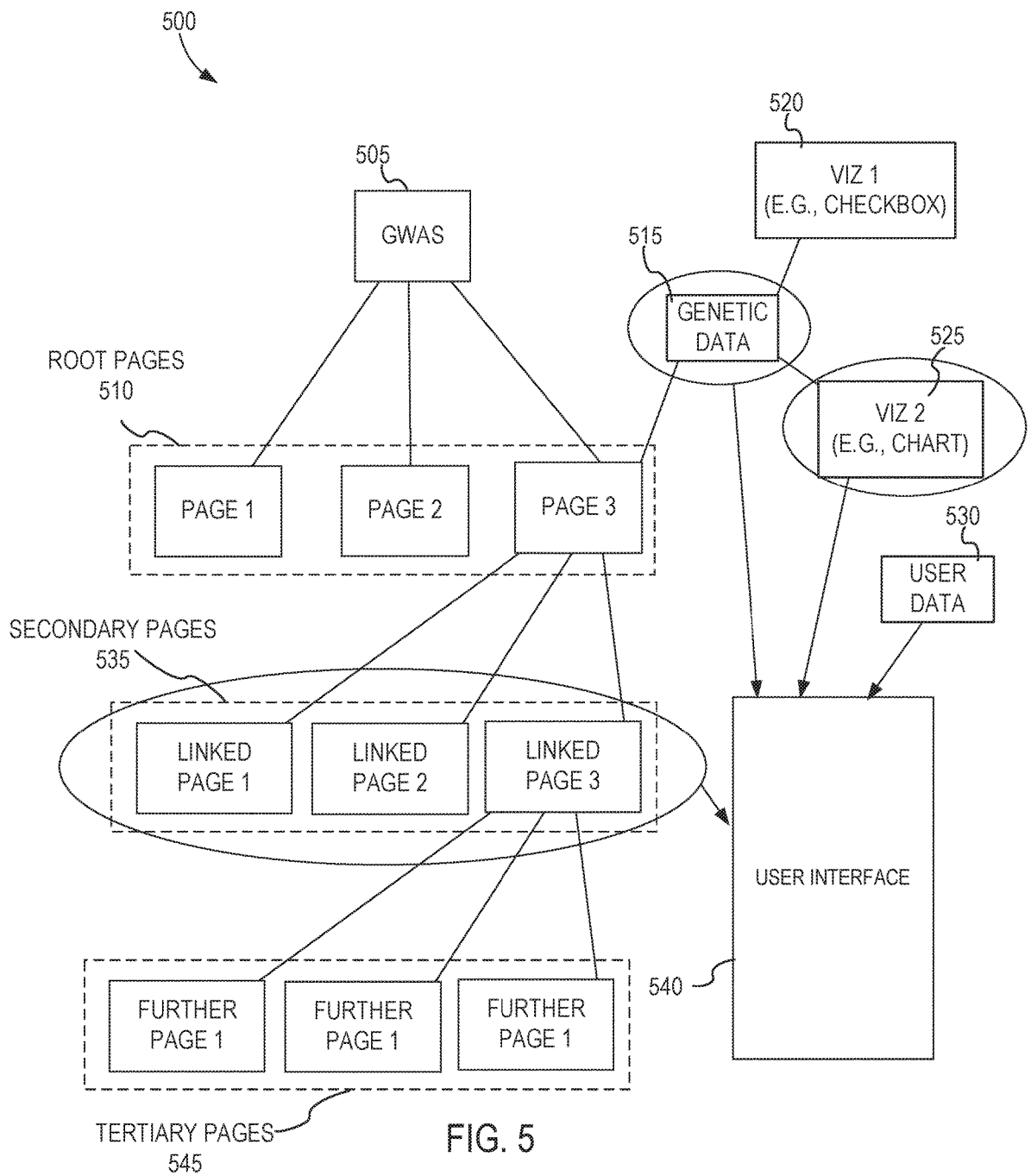
FIG. 5 which shows example data hierarchy and additional data structures, according to some example embodiments.

Attention is kindly directed to FIG. 5, which shows example data hierarchy 500 and additional data structures, according to some example embodiments. In FIG. 5, a genome-wide association study (GWAS) database 505 stores data from one or more GWAS studies. Generally, genome-wide association studies are conducted by leading researchers to compare the genotypes of large numbers of individuals to identify genetic variant data correlated with different genetic traits/expressions (e.g., infectious diseases, the ability to smell methanethiol after eating asparagus, etc.). The GWAS database 505 can contain entries for different studies published on a variety of different websites. In some example embodiments, a given root page may contain a link or entry referring to a GWAS data store (e.g., GWAS database 505). In some embodiments, one or more websites are pre-selected as being trusted sources of genomic data (e.g., www.nature.com). Pages that are hosted on the sites pre-selected as being trusted are root pages. In some example embodiments, the genomic update system stores the pre-selected websites and retrieves, from the GWAS database 505, only pages published on the pre-selected websites, such as one or more of the root pages 510. The websites are pre-selected in that they are of a trusted class of a network sites. Each of the root pages 510 of the pre-selected websites can comprise genetic variation data, such as genetic data 515.

Figure 6:
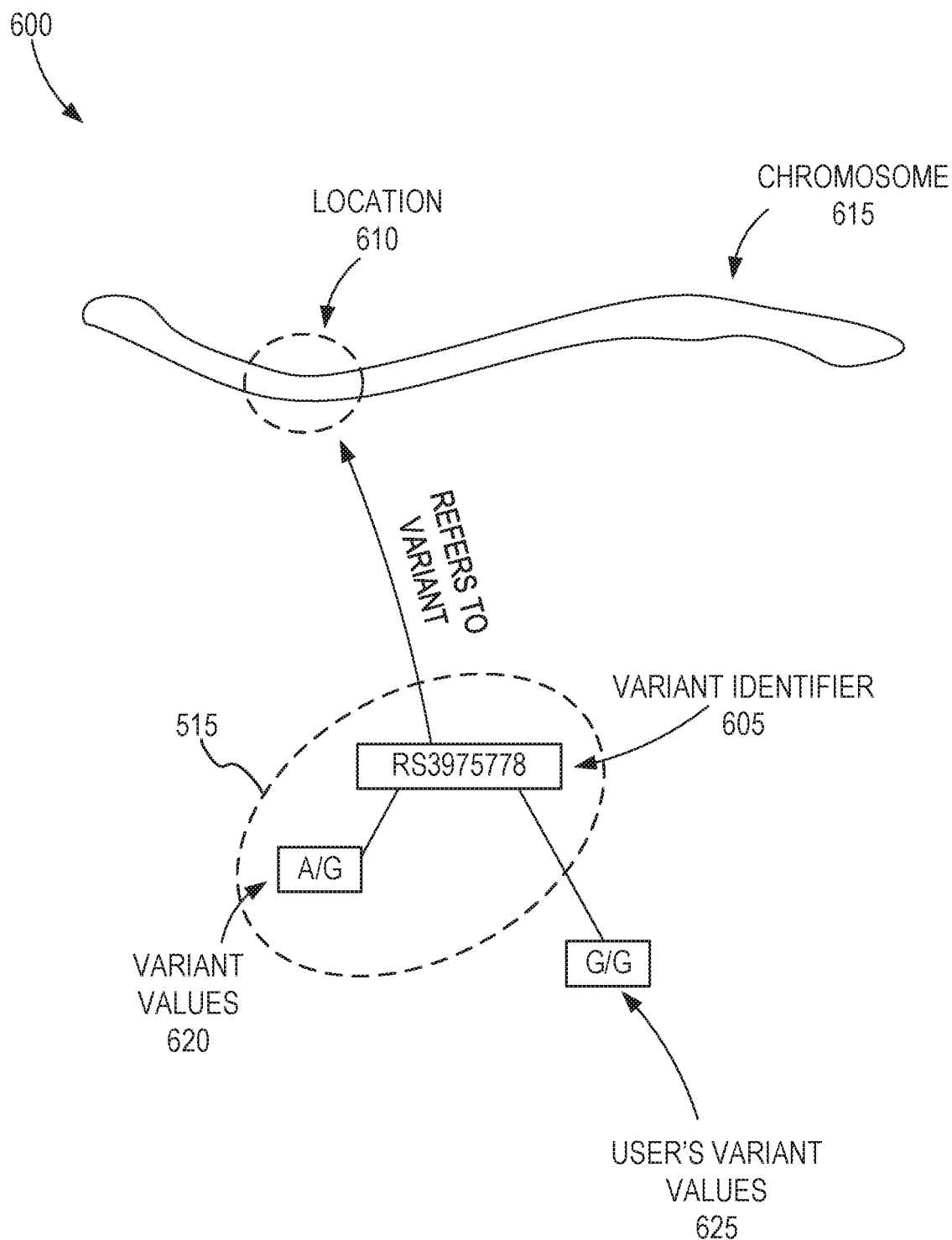
FIG. 6 shows an example of genetic data and user data values, according to some example embodiments.

FIG. 6 shows example data structures 600 that include genetic data 515 and user data 530, according to some example embodiments. As illustrated, the variant identifier 605 (e.g., BED location) is a key or an identifier of a genetic variation, such as a single nucleotide polymorphism (SNP) or multiple nucleotide variant (MNV). The variant identifier 605 identifies a genetic variation of genetic material, such as a chromosome 615 of the user. The variant occurs at a specific location 610 on the chromosome 615. In some example embodiments, the variant identifier 605 does not directly reference the location 610. In those example embodiments, the variant identifier 605 can be used as a lookup value to determine the variant location (e.g., start and stop window data, BED data, FIG. 4). The variant identifier 605 is associated with expected variant values 620 (e.g., "AG" alleles) which include the reference sequence as well as expected differences from the reference sequence.

A user that has their genetic data sequenced and stored in the genomic data storage 150 can compare their user variant values 625 to the variant values 620 of the variant identifier 605 to determine whether the user's variant values 625 match the variant values 620 of the genetic variation identified by the variant identifier 605. As discussed in further detail below, the user's variant values 625 need not exactly match the variant values 620 for the user to still exhibit the phenotype identified by the genetic variation of the variant identifier 605. For example, a study discussing the genetic variation of variant identifier 605 may explain that if the user contains a single variant value 620 of "G" (e.g.: "A/G") the user may have an increased likelihood (ex: 45%) of expressing the phenotype of the genetic variation, and a significant likelihood (ex: 90%) if the user contains two copies of the variant value "G" (e.g., "G/G"). However, even if the user's variant values 625 do not exactly match the variant values 620 (e.g., "T/G""), there still may be a significant statistical likelihood (e.g., around 45%) that the user will express the phenotype of the genetic variation.

Continuing the example with reference to FIG. 5, if the user data 530 is of a first match type (e.g., exact match) a first visualization 520 ("VIZ 1") is included in the user interface 540. On the other hand, if the user data 530 is of a second match type (e.g., a statistical match), a second visualization 525 ("VIZ 2") is included in the user interface 540. Additional visualizations likewise may be implemented, each type being pre-associated for inclusion in the user interface 540 based on a match type between the user data 530 and the genetic data 515.

As mentioned above, the root pages are trusted in that they are published to servers that have been pre-selected as scientifically trustworthy (e.g., Nature.com). Additional classes of pages hosted on other servers can be included in hierarchy 500. Further, content from those additional classes of pages can be included in a display if those pages have one or more links that point back to a root page. For example, with reference to FIG. 5, one or more of the root pages 510 may have links to secondary pages 535 that reference or link back to a given root page 510.

For example, "PAGE 3" of root pages 510 may have links to all three secondary pages 535, which may be pages of an elevated class (e.g., pages from newspaper websites). In some example embodiments, the secondary pages 535 are identified via spidering hyperlinks of a public network (e.g., the Internet) to determine which public network pages link to a given root page. Further, in some example embodiments, each root page 510 is parsed to extract link information to one or more secondary pages 535. For example, "PAGE 3" can be HTML parsed or "scraped" to identified network links to "LINKED PAGE 1", "LINKED PAGE 2", and "LINKED PAGE 3". In some example embodiments, if genetic data 515 from "PAGE 3" matches the user data 530, then one or more items of content from secondary pages 535 is included in the user interface 540 for display with a visualization, such as first visualization 520 ("VIZ 1").

Further, in some example embodiments, content from tertiary pages 545 that link to the secondary pages 535 can also be included in the user interface 540 if the user data 530 matches the genetic data 515 included in a root page 510, and further if a age in the tertiary class links to a page in the secondary class that in turn links to a root page. For example, if genetic data 515 from "PAGE 3" (in root pages 510) matches the user data 530, and if "PAGE 3" links to "LINKED PAGE 3" which further links to "FURTHER PAGE 3" (e.g., a blog, vlog, tabloid webpage, etc.) then one or more items of content from the "FURTHER PAGE 3" is included in the user interface 540 for display.

Figure 7:
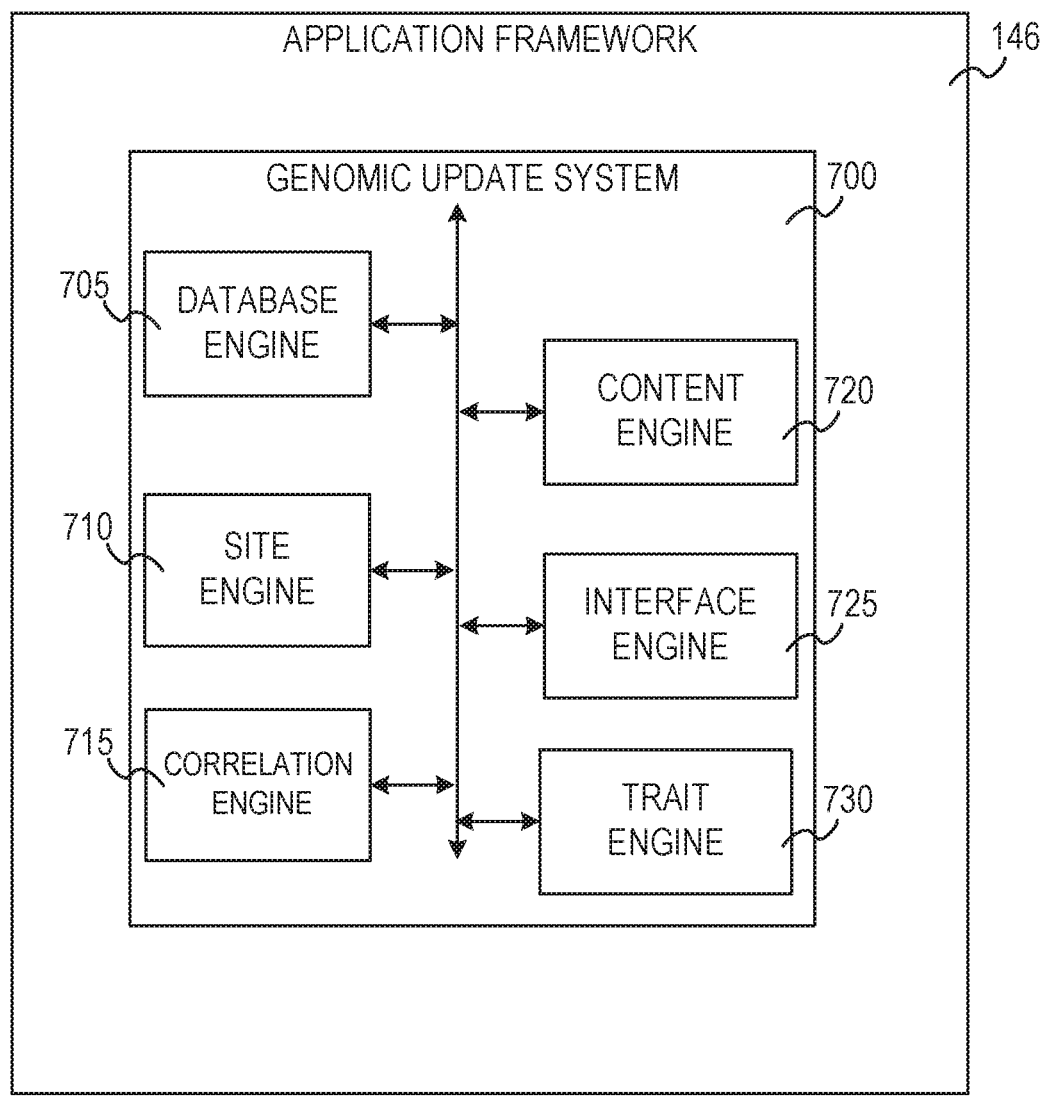
FIG. 7 shows example internal functional engines of a genomic update system, according to some example embodiments.

FIG. 7 shows example internal functional engines of a genomic update system 700, according to some example embodiments. The genomic update system 700 may be hosted and run from application server 146 in the system 100. However, in some example embodiments, the genomic update system 700 may be entirely run from a client device, such as client device 108, or from a partner application provider 120 (e.g., a server managed by partner application provider 120). Further, as discussed below, select engines of the genomic update system 700 may run on different devices, as discussed in further detail below with reference to FIG. 14.

As illustrated, the genomic update system 700 comprises a database engine 705, a site engine 710, a correlation engine 715, a content engine 720, an interface engine 725, and a trait engine. The database engine 705 is configured to access a database of genomic data, so such as a database storing genome wide association study (GWAS) data. In some example embodiments, the database that the database engine 705 accesses is stored internally in the genomic services platform 104 (e.g., in a partition of genomic data storage 150).

In other example embodiments, the database that the database engine 705 accesses is an external database that is programmatically accessible over a network using an API. In those example embodiments, the database engine 705 is configured to periodically poll or query for new updates to the external genomic database. For example, the database engine 705 can be configured to query the database for updates from sites that have been preselected as trusted sites (e.g., Nature.com, PLoS.com, sub-domains thereof, etc.), secondary sites, tertiary sites and so on, as discussed above with reference to FIG. 5. In some example embodiments, the database engine 705 is configured to store selections received from an administrative user of the system 100 of which sites are preselected sites. In those example embodiments, the database engine 705 may maintain its own internal database (e.g., in genomic data storage 150) such that the database only contains entries of network pages from pre-selected sites. Further, in some example embodiments, such as those using an external genomic database (e.g., an external GWAS database), the database engine 705 is configured to generate a query that specifies that only network pages from the preselected network server should be returned as query results.

The site engine 710 manages accessing the network pages identified by the database engine 705 from the genomic database, according to some example embodiments. In particular, for example, the site engine 710 may access or otherwise download the pages identified by the database engine 705 and extract data from the network pages. In some example embodiments, the site engine 710 is configured to extract one or more items of variant data (e.g., variant values 620, variant identifier 605, descriptive data that describes the genetic variation, etc.) of genetic variations described in the network pages. Further, in some example embodiments, the site engine 710 is configured to parse the network pages to extract network link data (e.g., hyperlinks) to pages that reference or mention a given network page, as described in further detail below.

The correlation engine 715 is configured to compare the variant values of the genetic variation reported in a given network page to the user's variant values to determine whether they match or otherwise correspond (e.g., statistically match). In some example embodiments, the correlation engine 715 determines whether the user's variant values exactly match the reported variant values, or statistically match the reported variant values.

The content engine 720 is configured to access and load additional network pages or content that is linked to the network pages, as discussed in further detail below. In some example embodiments, the content engine 720 can generate a summary or selection of a linked additional network page for inclusion in the user interface for display on the client device. Further, in some example embodiments, the content engine 720 is configured to identify a preselected visualization that has been pre-associated with the type of match identified by the correlation engine 715.

The interface engine 725 is configured to transmit network page data (e.g., pages of pre-selected servers), additional network page data (e.g., additional pages linked to the network pages), summarizing data (e.g., genetic variation data of the user), and or other data to a client device for display on a display screen of the client device. Further, in some example embodiments, in addition to the data values for display, the interface engine 725 transmits user interface markup language (e.g., HTML layout data, CSS data) for display within the client device (e.g., a web browser). In other example embodiments, the interface engine 725 transmits only the data values and not display/layout data, and the client device has native functionality for displaying the content in a user interface of an app, such as application 112 (FIG. 1).

The trait engine 730 is configured to manage correlations between network services (e.g., an application provided by the provider application provider 120) and pages published to a network site (e.g., a nature.com article). For example, when a newly published network page is identified, the trait engine 730 can identify one or more network services based on content in the network page and transmit a user interface displaying links to the network services to a client device.

Figure 8:
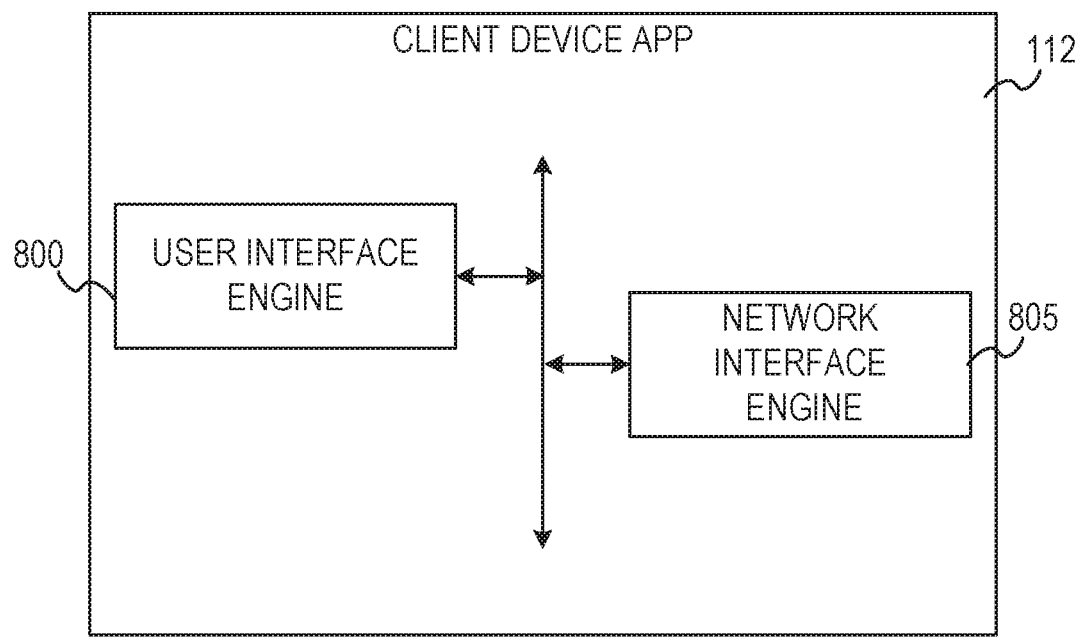
FIG. 8 shows example internal functional components of a client device application (e.g., mobile application), according to some example embodiments.

FIG. 8 shows example internal functional components of a client device application 112 (e.g., mobile application), according to some example embodiments. As illustrated, the client device application 112 comprises a user interface engine 800 and a network interface engine 805. The user interface engine 800 is configured to display one or more user interfaces on the client device application 112. In some example embodiments the user interfaces can include display elements such as selectable buttons (e.g., category buttons), scrollable windows (e.g., a newsfeed), images, text data, links to other user interfaces generated by the user interface engine 800, and/or links to external network sites.

The network interface engine 805 is configured to programmatically interact with the interface engine 725 of genomic update system 700. For example, the network interface engine 805 of the client device application 112 may receive genomic data of the user including network page data, visualizations, and/or content to display. The network interface engine 805 can be implemented as an API that programmatically receives raw data (e.g., no display/layout data) from the genomic update system 700 and transfers the data to the user interface engine 800 for display. Further, some example embodiments, the network interface engine 805 receives the raw data with display data (e.g., browser markup language) for display on the client device (e.g., a laptop's web-browser).

Figure 9:
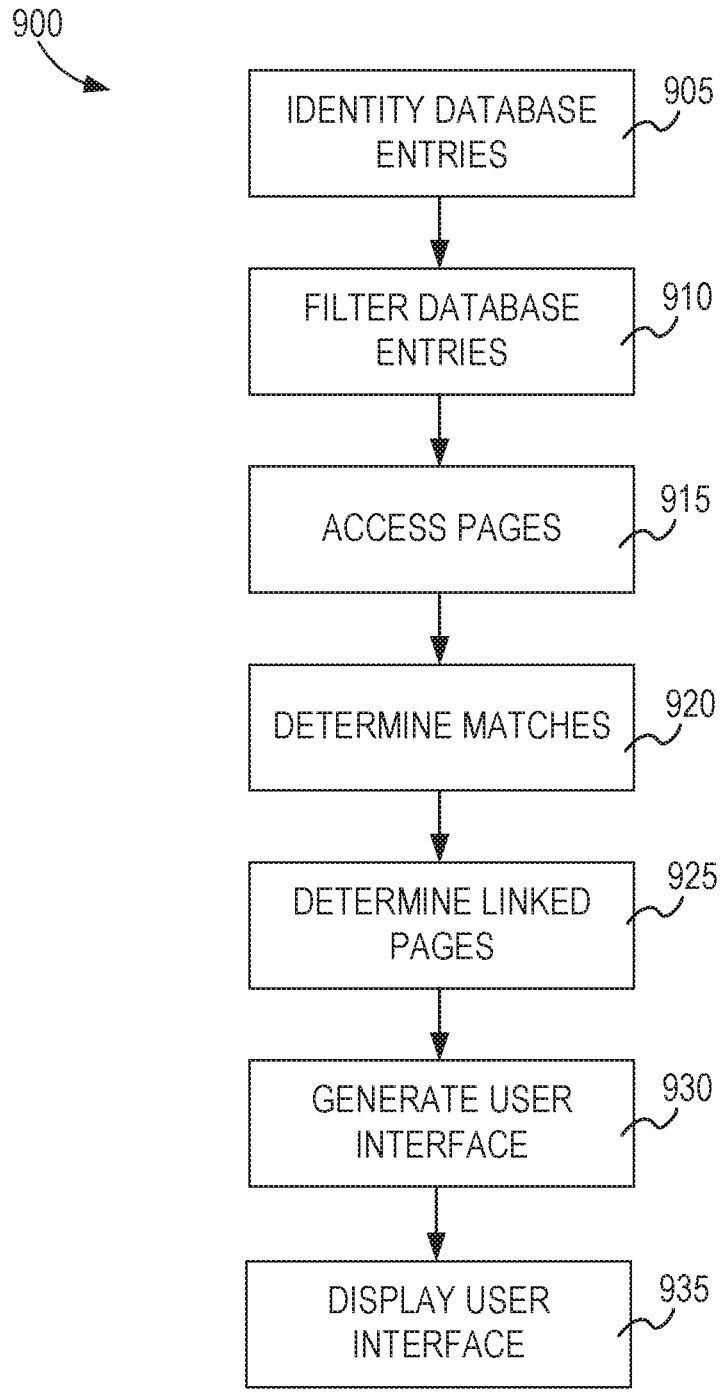
FIG. 9 shows a flow diagram of a method for implementing a genomic update user interface, according to some example embodiments.

FIG. 9 shows a flow diagram of a method 900 for implementing genomic update user interface, according to some example embodiments. At operation 905, the database engine 705 identifies database entries in a genomic database. For example, at operation 905, the database engine 705 queries an external GWAS database for updates. At operation 910, the database engine 705 filters the database entries. For example, the database engine 705 filters out network pages that do not originate from preselected servers. In some example embodiments, the GWAS database is an internal GWAS database that has been automatically created to ensure that network pages included as updates in the internal database are only from preselected servers. In those example embodiments, operation 910 may be skipped or otherwise omitted.

At operation 915, the site engine 710 accesses the network pages from the database results. For example, the database engine 705 may return a database update that indicates that one of the preselected servers has published a new network page describing a genetic variation breakthrough. In those example embodiments, the site engine 710 identifies a hyperlink to the network page hosted on the preselected server and downloads or otherwise accesses the network page for extraction of genetic variation data and network link data, as described in further detail below.

At operation 920, the correlation engine 715 compares the variant value data of the downloaded network page to the user's variant values from the genomic data storage 150 to determine whether the user's variant values match or otherwise satisfy the variant values reported in the network page, as described in further detail below.

At operation 925, the content engine 720 determines or otherwise identifies pages linked to the network page. For example, the network page that is downloaded from the preselected server may include one or more hyperlinks to websites that host pages that discuss or otherwise mentioned the network page from the preselected server. The content engine 720 may use HTML scraping or parsing to extract the link information and load the pages that are linked to the network page of the preselected server. Some example embodiments, the content engine 720 is configured to extract one or more portions of text (e.g., an abstract, an introduction paragraph) from the additional pages for display or inclusion in a genomic update user interface on the client device, as discussed in further detail below.

At operation 930, the user interface engine 800 generates a user interface comprising the network page data from the preselected servers, content from the additional pages that link to the network page that are not hosted from the preselected servers, one or more visualizations, and genetic data, as discussed in further detail below. At operation 935, the user interface engine 800 displays a user interface on the display device (e.g., a touchscreen display of a smartphone) of the client device 108.

Figure 10:
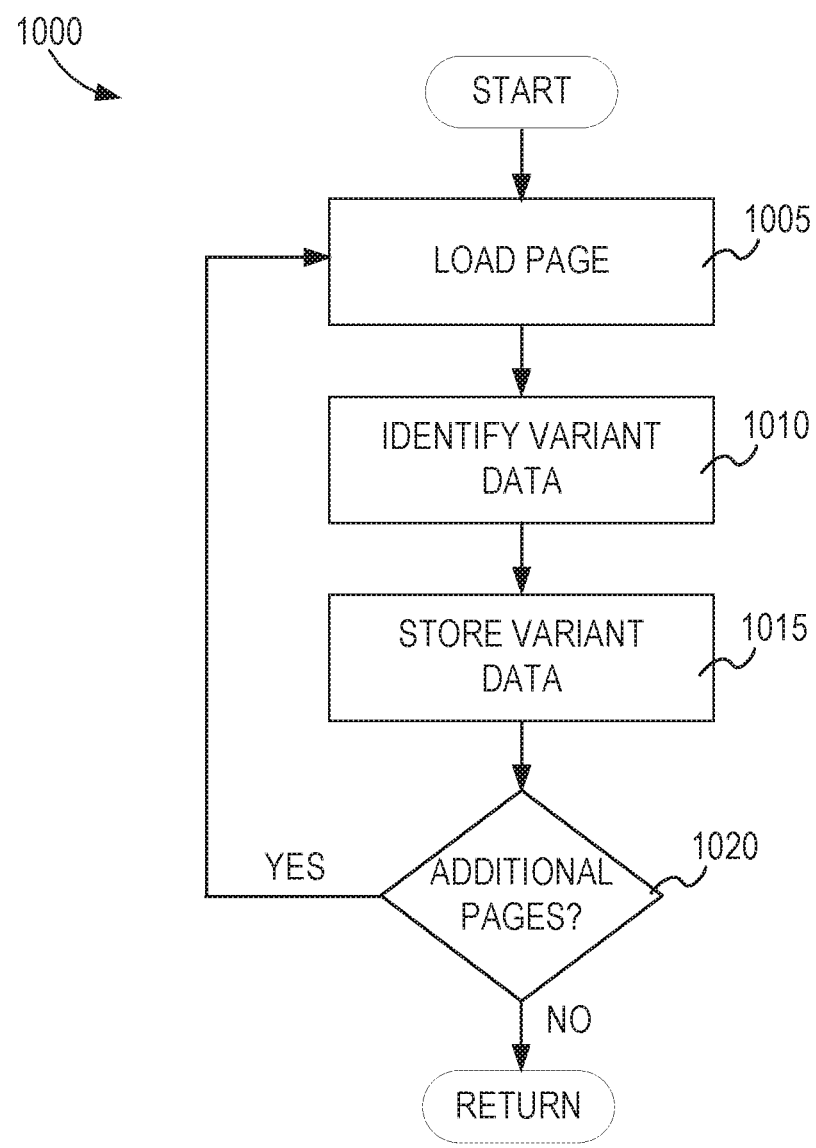
FIG. 10 shows a flow diagram of a method for identification storing of variant data from a network page of the preselected server, according to some example embodiments.

FIG. 10 shows a flow diagram of a method 1000 for identification storing of variant data from a network page of the preselected server, according to some example embodiments. The operations of method 1000 may be implemented as a subroutine of operation 915 of method 900 in which network pages hosted on preselected servers are accessed and parsed for variant data. In some embodiments, multiple network pages from preselected servers are identified at operations 905 and 910. In the example of FIG. 10, the subroutine method 1000 is configured to loop through each page and store variant data (e.g., with reference to FIG. 6, one or more variant identifiers such as variant identifier 605, one or more variant values such as variant values 620) for analysis in comparison to user variant values. At operation 1005, the site engine 710 loads a network page from preselected server. For example, at operation 1005 the site engine 710 downloads a webpage of a journal article from a trusted scientific website.

At operation 1010, the site engine 710 identifies variant data in the loaded page. For example, at operation 1010, the site engine 710 performs a keyword search for genetic variation identifiers (e.g., an RSID of SNP variation). In some example embodiments at operation 1010, the site engine 710 searches a loaded page for the variant identifier data by searching for an alphanumeric data in a pre-specified format. For example, at operation 1010, the site engine 710 may search loaded page for an alphanumeric term comprising two letters (e.g., "rs") followed by at least one integer.

Further, at operation 1010, the site engine 710 identifies the underlying variant values of the identify genetic information. At operation 1015, the site engine 710 stores the extracted variant data in a database such as genomic data storage 150. At operation 1020, the site engine 710 determines whether there are additional network pages of preselected servers that were identified otherwise returned as query results from a database (e.g., a GWAS database). If there are additional pages for parsing, the method 1000 loops to operation 1005 for parsing of additional pages. After the pages in the return set have been parsed, the subroutine terminates or otherwise returns to the method 900 of FIG. 9.

Figure 11:
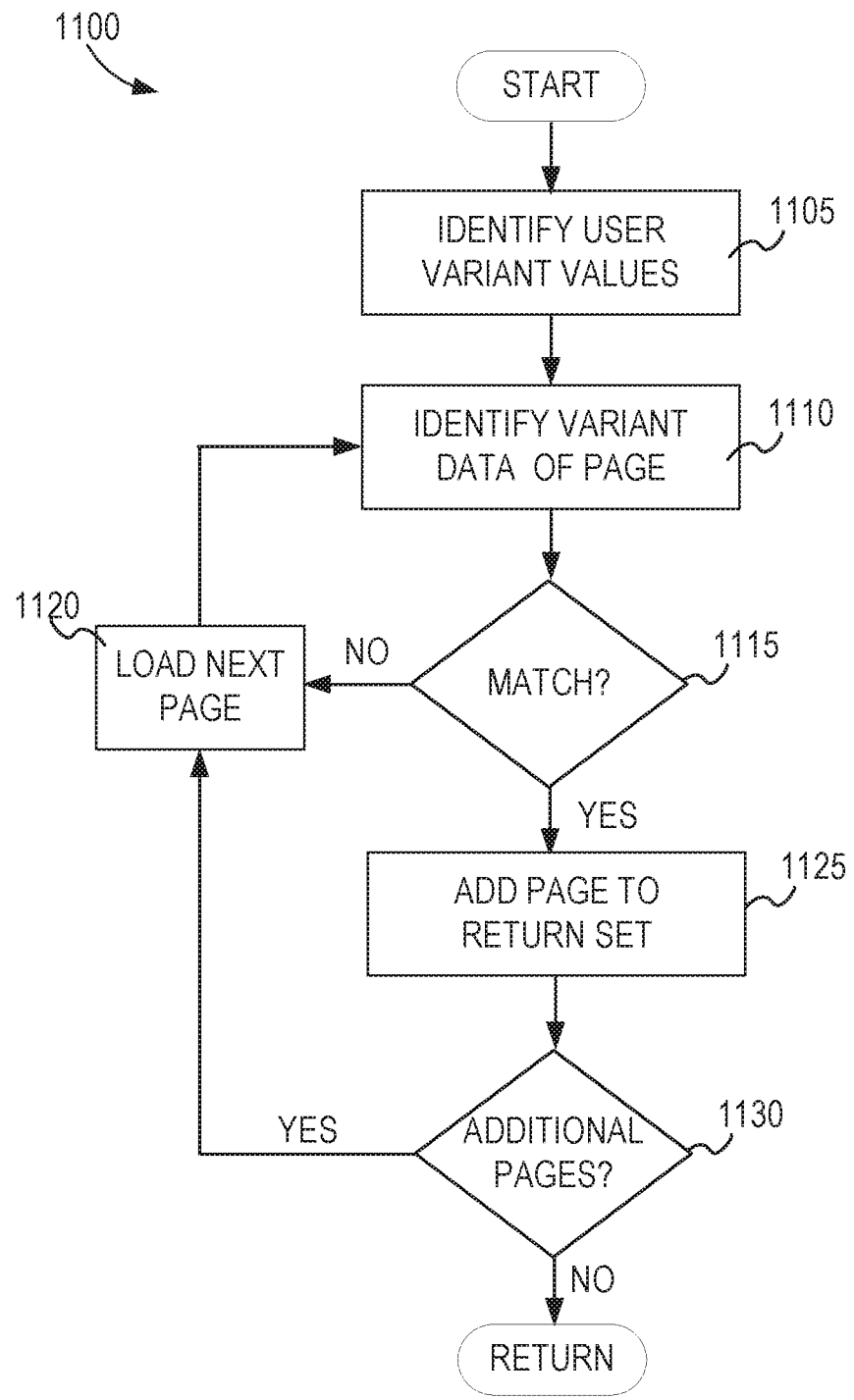
FIG. 11 shows a flow diagram of a method for determining matches of user variant values to variant values of network pages of preselected servers, according to some example embodiments.

FIG. 11 shows a flow diagram of a method 1100 for determining matches of user variant values to variant values of network pages of preselected servers (e.g., root pages), according to some example embodiments. The operations of method 1100 may be implemented as a subroutine of operation 920 in FIG. 9. At operation 1105, the correlation engine 715 identifies user variant values. For example at operation 1105, the correlation engine 715 identifies the variant identifier (e.g., an RSID, such as variant identifier 605) and determines the relevant location of the variants on the user's genome using the variant storage module 154. The correlation engine 715 then requests and receives the user variant values (e.g., user variant values 625, FIG. 6) for comparison.

At operation 1110, the correlation engine 715 identifies the variant value data of a root page of a preselected server. For example, at operation 1110, the correlation engine 715 identifies variant values 620 (FIG. 6) that have been parsed from one of the root pages of the preselected servers. At operation 1115, the correlation engine 715 determines whether the user variant values match the variant values from the root page of the preselected servers. As discussed, matching can include an exact match, a statistical match, or other types of matching (e.g., comparison to a population's average value). If the user's variant values do not match the root page's variant values, then at operation 1120 the correlation engine 715 loads the next root page and the method 1100 loops until the user's variant values match a given root page's variant values.

On the other hand, at operation 1115, when the user variant values match variant values of a root page, the correlation engine 715 adds the root page data (e.g., address, variant data, etc.) to the return set at operation 1125. At operation 1130 the correlation engine 715 determines whether there are additional root pages for analysis. If there are additional root pages for analysis, the method 1100 loops to operation 1120 in which the next root page is loaded for comparison to the user's variant values. In this way, the method 1100 loops through all the network pages until all root pages that have variant values that match a user's variant values have been added to the return set.

Figure 12:
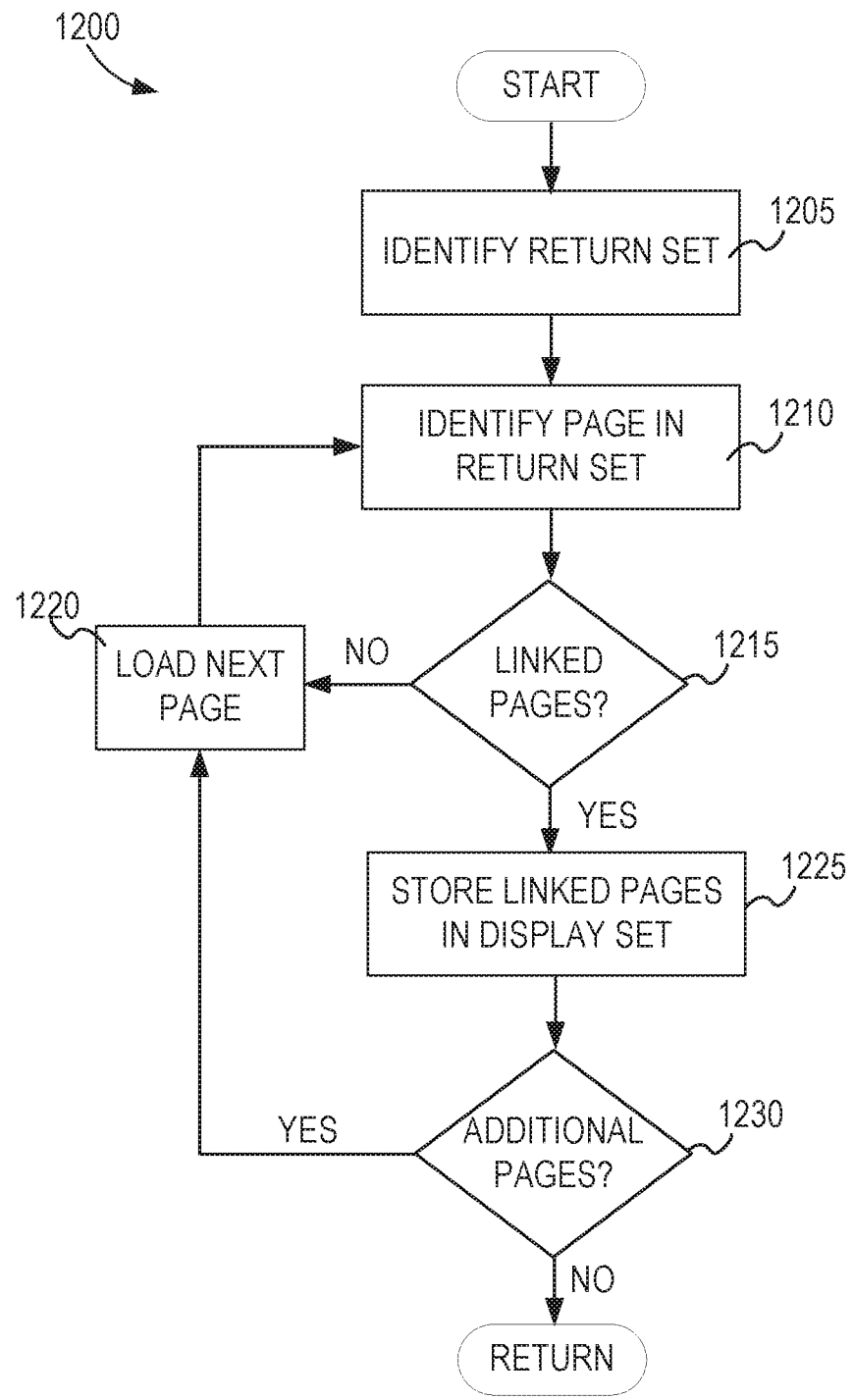
FIG. 12 shows a flow diagram of a method for identifying page content for inclusion in the user interface, according to some example embodiments.

FIG. 12 shows a flow diagram of a method 1200 identifying page content for inclusion in the user interface, according to some example embodiments. The method 1200 can be implemented as a subroutine of operation 925 of method 900 in FIG. 9. If implemented as a subroutine, the method 1200 starts with a start block and ends or otherwise terminates with a return block in which data is stored for processing in method 900. At operation 1205, the content engine 720 identifies the return set of pages that were determined by the site engine 710 to match the user variant values, as discussed above with reference to FIG. 11. At operation 1210, the content engine 720 identifies one of the root pages in the return set. For example, at operation 1210, the content engine 720 accesses or downloads a given root page in the return set from a network server that hosts the root page (e.g., www.nature.com). At operation 1215, the content engine 720 determines whether the identified root page contains network links to additional pages, such as secondary pages 535 that are hosted on servers that are not in the preselected server set. If the identified root pages do not contain additional links, the next root page in the return set is loaded at operation 1220 and the method 1200 loops until a root page having additional links is identified. In some example embodiments, the additional links are identified using markup language layer parsing (e.g., page scraping, HTML page scraping, XML page scraping, markup tag analysis).

At operation 1225, the content engine 720 stores the linked pages or portions of the linked pages in the display set. For example, at operation 1225 the content engine 720 may store the content of a given link page, such as the first paragraph for use as a summary or introduction for an item of content in a user interface. At operation 1230, the content engine 720 determines whether there are additional root pages for link identification and content parsing. If there are additional root pages for processing, the method 1200 continues to operation 1220 in which the next additional root page in the return set is process. If there are no additional root pages for processing, the method 1200 terminates or otherwise stores data for return to method 900.

Figure 13:
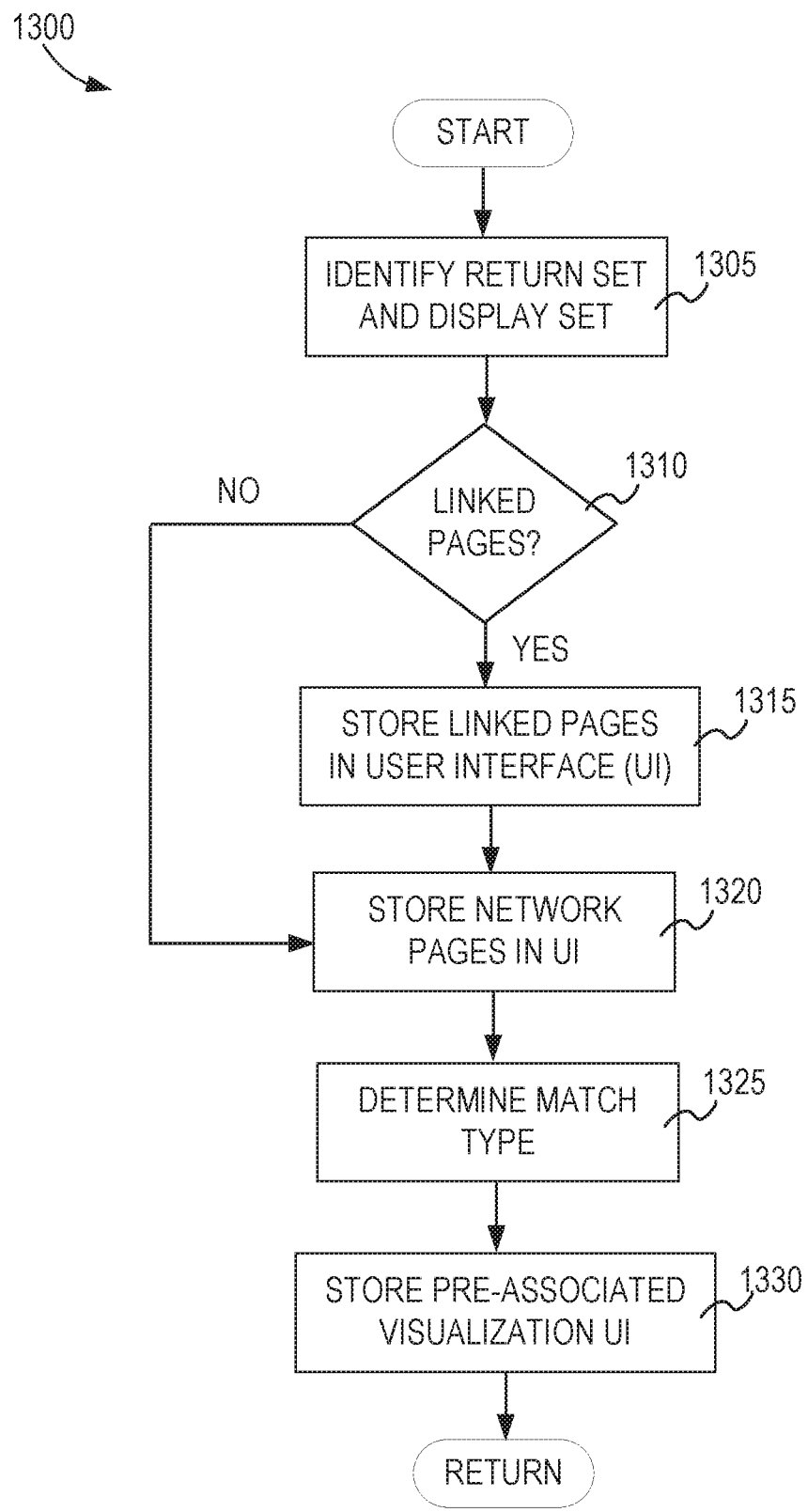
FIG. 13 shows a flow diagram of a method for identifying associated content for display in a genomic user interface, according to some example embodiments.

FIG. 13 shows a flow diagram of a method 1300 for identifying associated content for display in a genomic user interface, according to some example embodiments. The method 1300 can be implemented as a subroutine of operation 925 of method 900 in FIG. 9. If implemented as a subroutine, the method 1300 starts with a start block and ends or otherwise terminates with a return block in which data is stored for processing in method 900.

At operation 1305, the content engine 720 identifies the return set, which comprises one or more root pages, and the display set, which comprises pages that link to one or more of the root pages. At operation 1310, the content engine 720 determines whether each of the root pages is associated with a linked page. If a given root page does not have an associated linked page (e.g., the root page does not link to a linked page, or no published webpage links or references the given root page), the content engine 720 falls back and, in operation 1320, stores the root page for inclusion in the user interface. In this way, if a given genetic variation does not have additional linked pages (e.g., an easier to read newspaper webpage article, blog page), the user interface can at least include data content from the root page as a fallback mechanism.

In contrast, at operation 1310 if a given root page is linked or otherwise associated with one or more link pages, the content engine 720 stores the linked pages for inclusion in the user interface at operation 1315. In some example embodiments, even if a root page is associated with a linked page, the root page is nonetheless included in the user interface at operation 1320. Further, in other example embodiments, if a root page is associated with a linked page, the method 1300 skips to operation 1325 and the root page is not included in the user interface display to the end user.

At operation 1325, the content engine 720 determines how the user variant values match the variant values described in the root page. For example, if the user variant values exactly match the variant values described in every page, a first type of visualization (e.g., a checkbox) may be included in the user interface for display with the genetic variation data in the linked page. As an additional example, if the user variant values do not exactly match the variant values in the root page but nonetheless a significant portion of the population reports exhibiting the phenotype described by the variant values in the root page, the match type is nonetheless considered statistically significant, and a different visualization communicating the uncertainty or likelihood of phenotype expression can be included in the visualization user interface at operation 1330.

Figure 14:
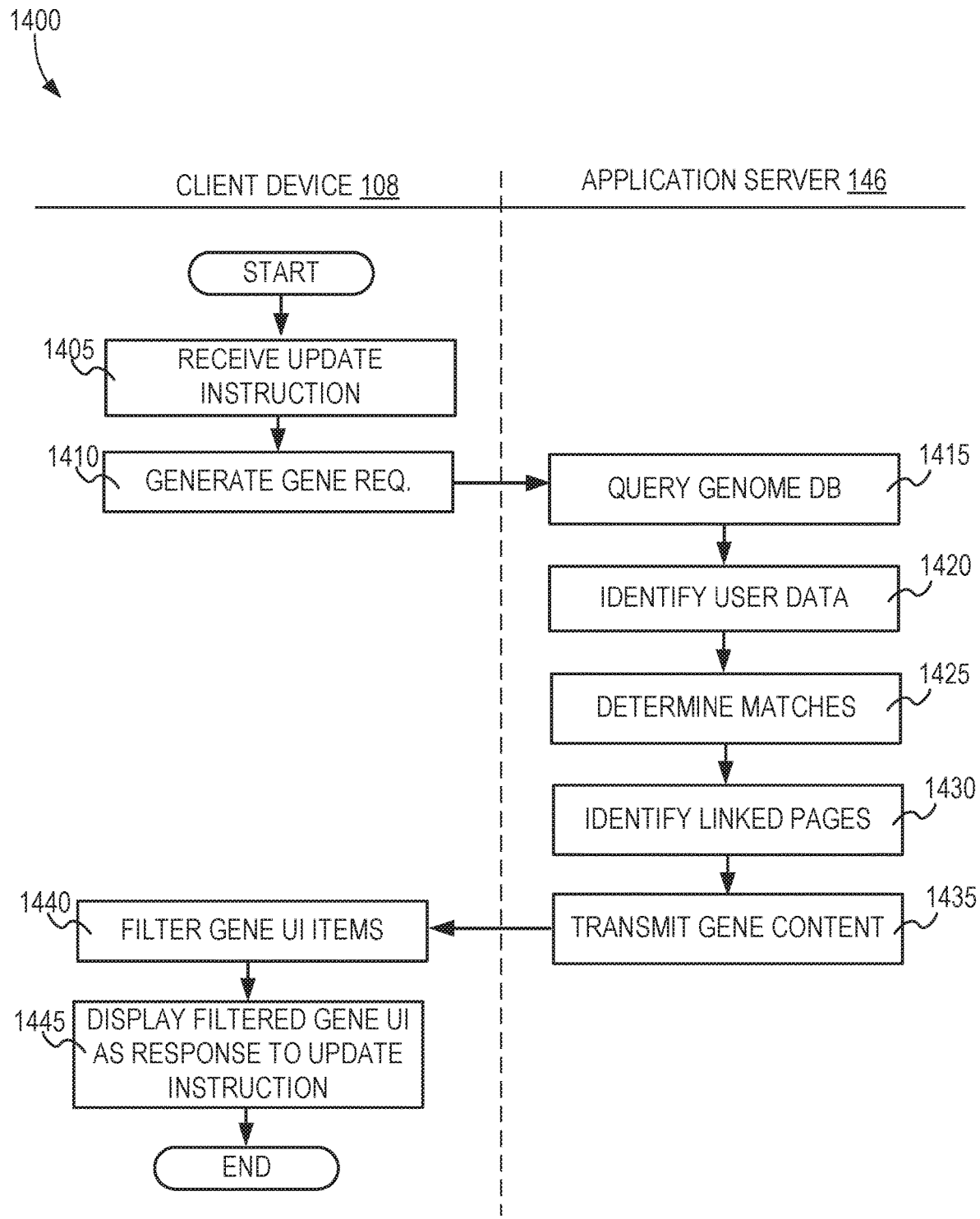
FIG. 14 shows a network interaction diagram implementing a genomic update user interface, according to some example embodiments.

FIG. 14 shows a network interaction diagram 1400 implementing a genomic update user interface, according to some example embodiments. The operations on the left side of the dotted line are performed by the client device 108, whereas the operations on the right side of the dotted line are performed by other network devices such as the application server 146 or third-party network servers (e.g., partner application providers $120_{1-N}$). At operation 1405, the user interface engine 800 (that is executing on the client device 108) receives an update instruction. For example, a user of the client device 108 selects a button or performs a gesture that triggers a genomic update operation. At operation 1410, the network interface engine 805 generates a genomic update request and transmits the genomic update request to the interface engine 725 (that is executing on the application server 146). In some example embodiments, the request generated at operation 1410 includes a user identifier (e.g., user account data) but does not include any of the user's genetic data and/or data that can be used to identify the user. In some example embodiments, the communications between the client device 108 and the application server 146 are encrypted through one or more encryption mechanisms (e.g., HTTPS, application level encryption) to ensure user privacy.

In response to the request, at operation 1415, the database engine 705 queries a genome database (e.g., a GWAS database). As discussed above, in some example embodiments, the database query by the database engine 705 is an internal database that comprises only root pages from preselected servers in a trusted class. In those example embodiments, the query can request any update to the internal databases. Further, as discussed above, in some example embodiments, the database engine 705 queries an external database that stores genome data for any updates of root pages that originate from servers that are in the preselected class. At operation 1420, the correlation engine 715 identifies user variant data (e.g., user variant values 625, FIG. 6). At operation 1425, the correlation engine 715 determines whether the user's variant data match any of the variance values of the genetic variations described in the root pages. At operation 1430, the content engine 720 identifies linked pages that link back to or otherwise reference any of the root pages. As discussed above, in some example embodiments, the linked pages are identified via links included in a given root page. Further, in some example embodiments, the linked pages are pages that are found through spidering a public network (e.g., the Internet). In some example embodiments, the additional pages in a secondary elevated class or a tertiary class are submitted by third parties for validation by the content engine 720. For example, a partner application provider 120 can submit a page of content that references a secondary elevated class page or a root page. In those example embodiments, the content engine 720 can determine whether the submitted page of content links publicly on the Internet to one of the root pages. If so, the submitted page can be included for potential display in the user interface, according to some example embodiments. At operation 1435, the interface engine 725 transmits the genetic content through a secure channel to the network interface engine 805 executing on the client device 108.

At operation 1440, according to some example embodiments, the user interface engine 800 filters the received items based on categorical selections from the user, or default categorical selections. For example, if the user account data indicates that the user is below a certain age, one or more items of content in a class may be filtered out. For instance, if the user is below 12 years old, a more technical scientific article in a secondary elevated class may be filtered out at operation 1440. At operation 1445, in response to the update instruction received at 1405, the user interface engine 800 displays the genomic content in a genome update user interface operating on the client device 108.

Figure 15:
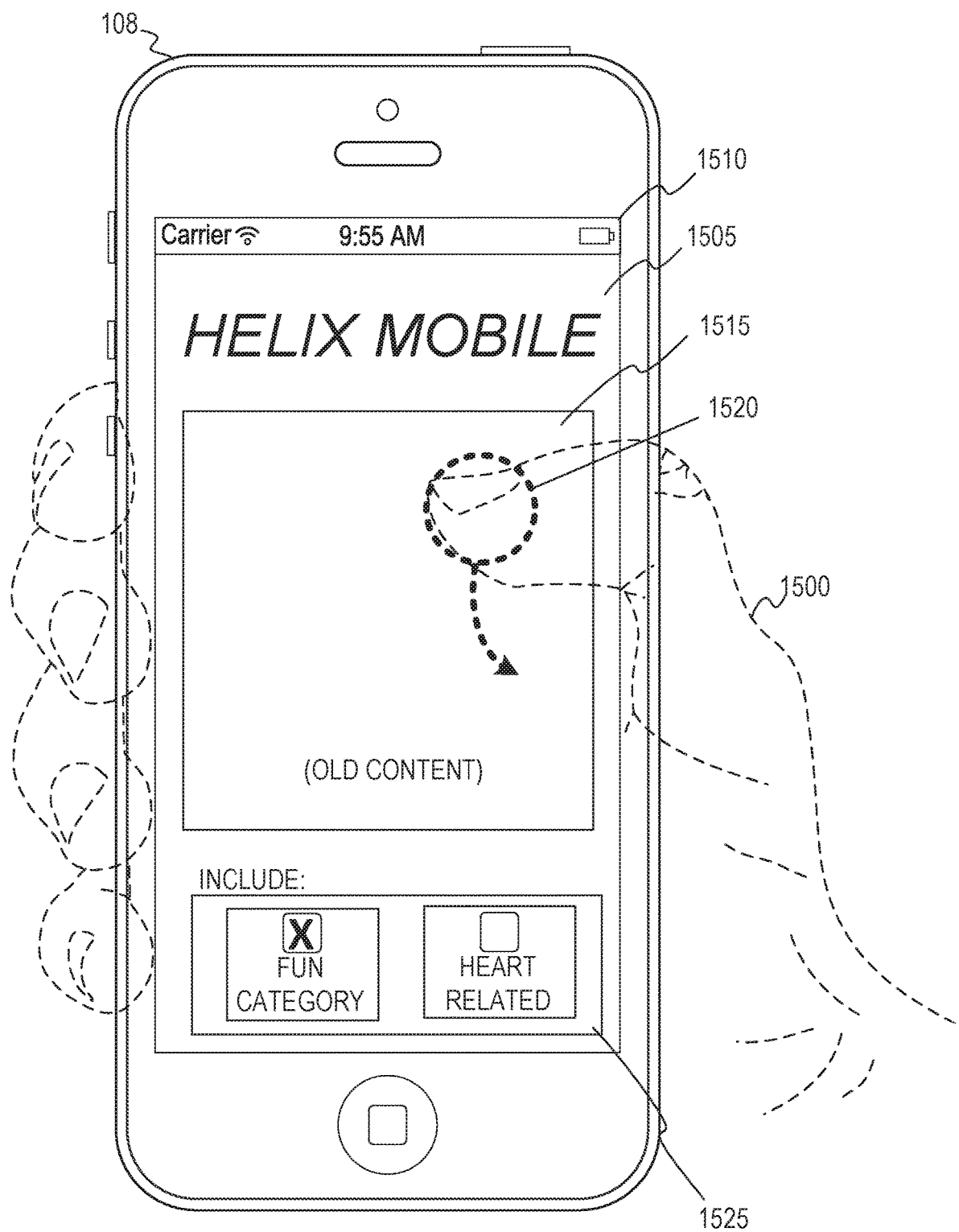
FIG. 15 shows an example genomic update user interface, according to some example embodiments.

FIG. 15 shows an example genomic update user interface 1505, according to some example embodiments. As illustrated in the example of FIG. 15, a user 1500 is holding a client device 108 having a touchscreen display 1510 currently displaying the genomic update user interface 1505. The genomic update user interface 1505 comprises one or more items of old content 1515 (e.g., content that was retrieved and displayed during past genomic update operations). The genomic update user interface 1505 further displays category selection elements 1525. The category selection elements 1525 include a fun category that has been selected by the user 1500 and a more serious heart-related category. In the example of FIG. 15, the user 1500 generates the instruction to retrieve genomic updates for the fun category by performing an input operation, such as gesture 1520, by swiping down on the touchscreen display 1510.

Turning to FIG. 16, in response to the user's genomic update instruction, a genome database 1600 is queried by the database engine 705 for updates. As displayed in FIG. 16, the genome database 1600 comprises entries 1605-1620. Each of the entries 1605-1620 can correspond to a root page published on a site, such as a preselected site. For example, entry 1605 may be an entry in the genome database 1600 that links to a root page that originates from a preselected site, such as nature.com, while the other entries 1610 to 1620 may not be pages published or otherwise originating from a preselected network site.

FIG. 17 shows an example root page 1700 that can be accessed or otherwise loaded by site engine 710. As illustrated, the root page 1700 is a scientific article comprising genetic variation data 1705 that is buried in complex scientific text (in 1705, the "RS" in "RS3975778" may be listed in lower case, e.g., rs3975778, according to some example embodiments). The root page 1700 further includes additional links 1710, which are network links to additional pages such as pages from an elevated secondary class or tertiary class as discussed above.

Figure 18:
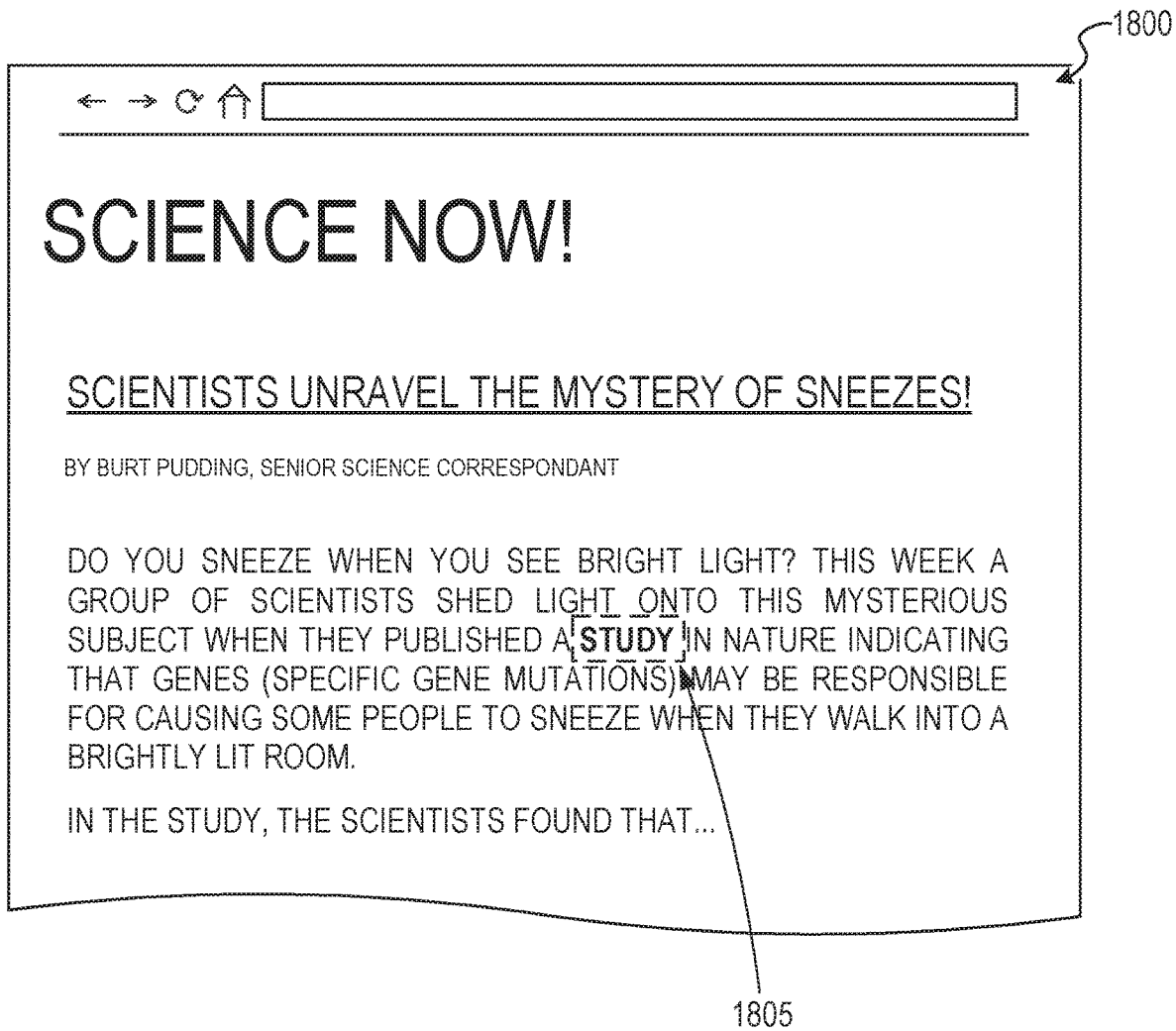
FIG. 18 shows an example of a linked page that links or otherwise references a root page, according to some example embodiments.

FIG. 18 shows an example of a linked page 1800 that links or otherwise references a root page, according to some example embodiments. As discussed above, in some example embodiments, the content engine 720 may identify the linked page based on a link extracted from the root page, or through spidering and/or other means (e.g., third-party submission). In the example of FIG. 18, the linked page 1800 comprises a hyperlink 1805 that comprises an address link to root page 1700, according to some example embodiments. The content engine 720 may store the address of the linked page 1800, images of the linked page 1800, or exits of the linked page for inclusion in the user interface.

Figure 19:
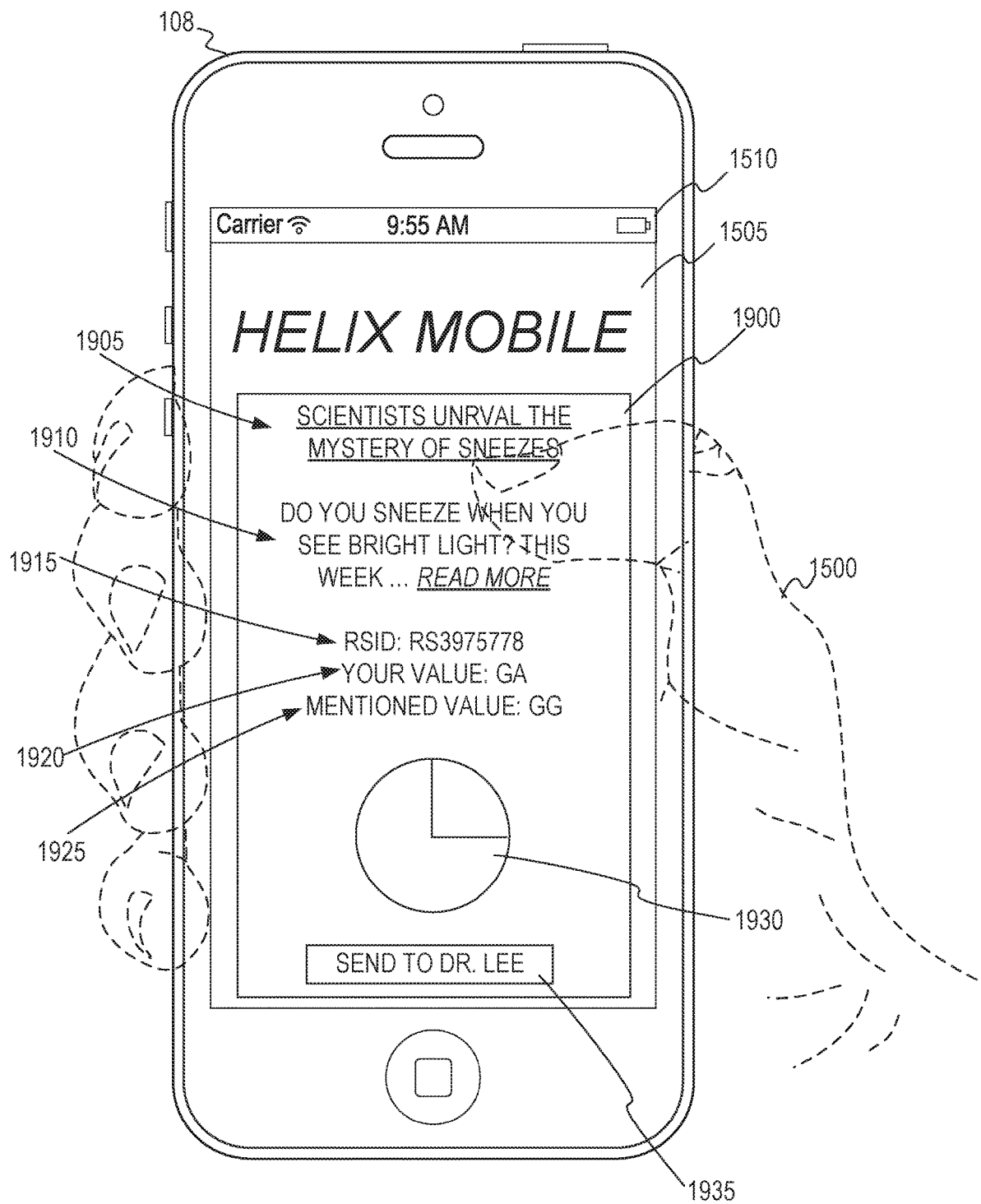
FIG. 19 shows an updated genomic user interface, according to some example embodiments.

FIG. 19 shows an updated genomic update user interface 1505, according to some example embodiments. As illustrated, in response to the user 1500 issuing the genomic update instruction, updated user interface content 1900 is displayed on the client device 108. The updated user interface content 1900 may contain the title 1905 of the linked page 1800, an excerpt 1910 of the linked page 1800, a genetic variant identifier 1915 (from the root page 1700), user variant data 1920, variant data 1925 (from the root page 1700, FIG. 17), and a visualization 1930 (e.g., a pie chart) that has been selected based on how the user variant data 1920 matches the variant data 1925. The updated user interface content 1900 can further include a communication element 1935 is configured to generate an electronic message for transmission to a medical professional. The generated electronic message may include data from the root page 1700 and user data (deceased e.g. user variant values). In some example embodiments, the genomic update user interface 1505 is configured as a scrollable newsfeed in which multiple items of content can be more readily navigated by the user 1500 using the client device 108 in one hand.

Figure 20A:
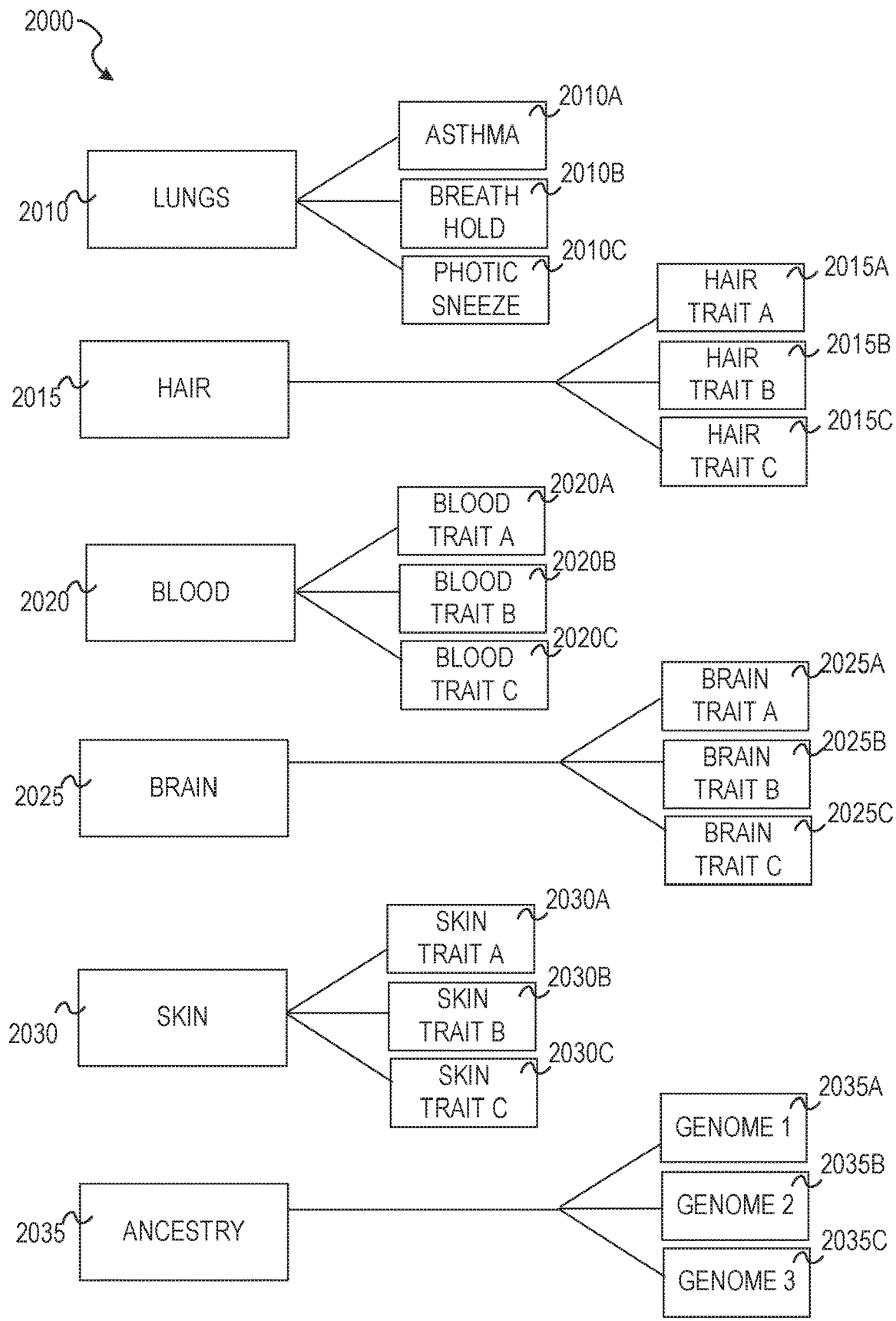
FIGS. 20A and 20B show example trait database structures, according to some example embodiments.

As discussed above with reference to FIG. 7, the trait engine 730 manages identifying genomic content based on genetic variation data included in root pages or GWAS database items. Genetic content includes root pages, pages linked to the root pages, and network services, according to some example embodiments. The network services can include applications provided, hosted, or otherwise accessed through partner application providers (e.g., partner application providers 120). The partner applications providers have selective access to different portions of user genomic data to provide intricate analysis, visualizations, and advanced analysis of accessible portions of a given user's data. Which network service is associated with a given network page can depend on a type of access granted or analysis provided by the network service. In some example embodiments, when a user's data is sequenced and stored in genomic data storage 150, the trait engine 730 can identify one or more network services for inclusion in a user interface displayed to the user. In some embodiments, the trait engine 730 identifies network services via a database, such as trait data structure 2000, as displayed in FIG. 20A.

The trait data structure 2000 includes trait categories 2010-2035, which group similar observable traits (e.g., phenotypes). For example, trait category 2010 is a lung trait category comprising subcategory 2010A (asthma specific genetic traits), subcategory 2010B (breath holding specific genetic traits), and subcategory 2010C (photic sneeze specific genetic traits). Likewise, trait category 2020 is a blood trait category comprising subcategories 2020A-C for different blood specific genetic traits. Further, trait category 2025 is a brain trait category comprising subcategories 2025A-C for different brain specific genetic traits, and trait category 2030 is a skin trait category comprising subcategories 2030A-C for different skin specific genetic traits. Further, according to some example embodiments, trait categories can comprise ancestry or inheritance data (e.g., ancestry origins data, haplogroup data, ancient genomes data). For example, trait category 2035 is an ancestry related category including genome data of different genomes, such as genome subcategories 2035A-C.

Each of the categories in trait data structure 2000 can be associated with metadata items and content items, as illustrated in expanded category data 2050 (FIG. 20B), which shows expanded associations of the trait category 2010 (lung category). Each of the subcategories can be associated with root pages, additional pages that link to the root pages, and one or more network services. For example, category 2010A is an asthma category, which links to a root page 2052 (e.g., a study in a webpage from pre-selected servers), additional page 2054 (e.g., a news website article page) that links to the root page 2052, and multiple network services 2056 which are network links to partner application providers 120.

The other subcategories that link to category 2010 likewise have associated items that are related to lung specific traits. For example, subcategory 2010B is a breath holding category that is associated with root page 2058 (e.g., a study hosted on pre-selected servers) describing a potential genetic predisposition for the ability to hold one's breath for long periods of time, additional page 2060 (e.g., a blog article) that links to the root page 2058, and an associated network service 2062 (e.g., a network link to a partner application provider network site). Likewise, subcategory 2010C is a photic sneeze category describing a genetic trait or phenotype of sneezing in response to light changes. Subcategory 2010C is associated with network service 2064, and further associated with additional page 2066 (e.g., a press release webpage), which cites root page 2068 (e.g., a study).

Figure 20B:
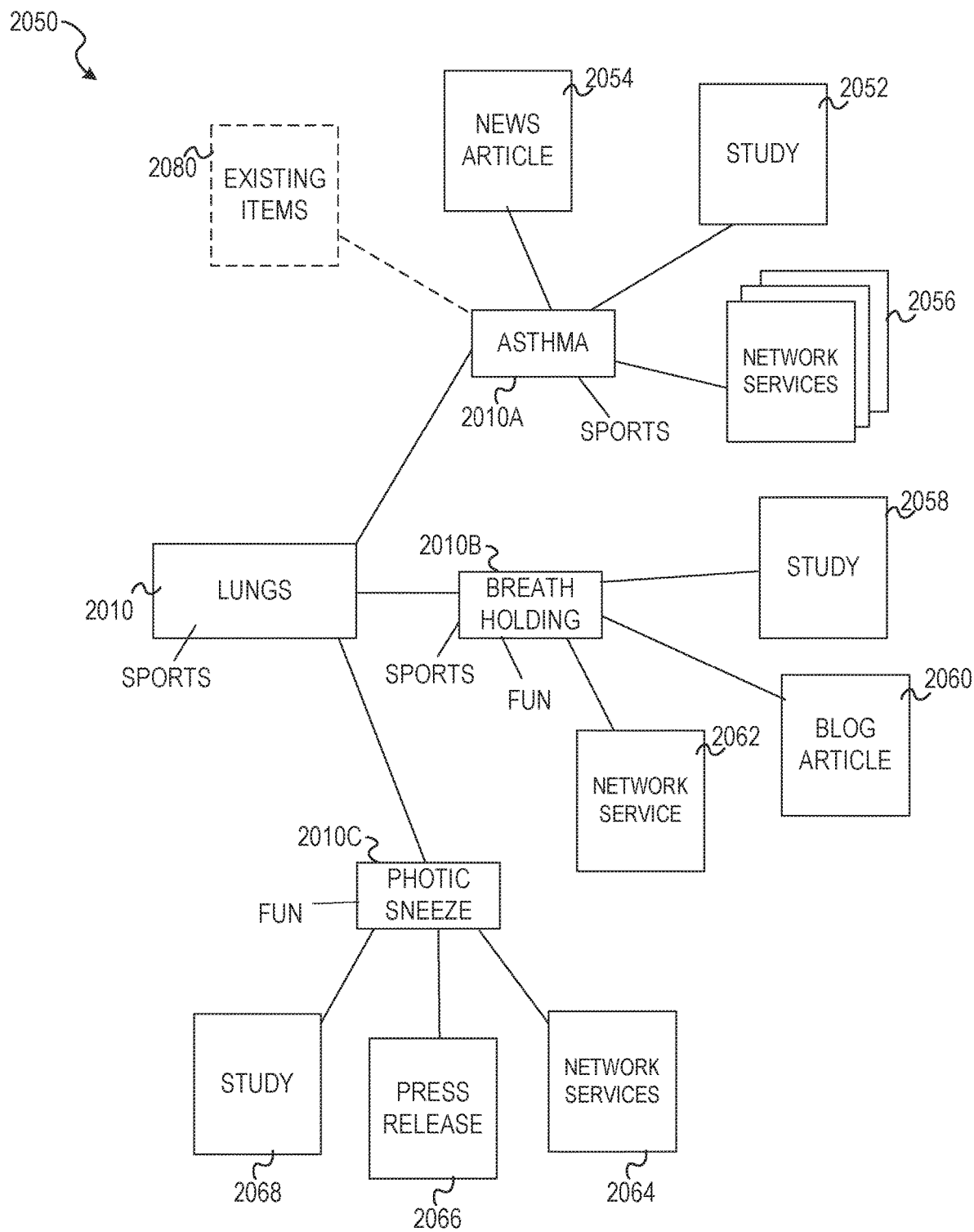

Each of the categories can have metadata items tags that can be implemented to filter suggested network services or content items based on user selections input via category selection elements 1525. For example, if a user selects a sports category, then items from subcategory 2010A or 2010C are included in the display as those subcategories both have metadata sports tags. Further, top level categories, such as category 2010, can include metadata tags. For example, as illustrated in FIG. 20B, category 2010 can have a sports metadata tag. If a user selects a sports category, then all underlying subcategory items (e.g., multiple network services 2056, root page 2068) can be included for display.

In the example illustrated in FIG. 20B, a single root page and a single additional page are associated with each subcategory. It is appreciated that each subcategory can be further associated with additional previously generated items, such as existing items 2080, which may include existing root pages and additional pages that link to the root page. The existing items 2080 may be automatically included for display in a user interface when network services 2056 are included in the user interface, according to some example embodiments. In some example embodiments, the additional pages are replaced by a brief description that summarizes the additional page content or the root page content. In those example embodiments, when a given network service that is related to a rooted page is included in the display, the short description of the additional page linked to the root page is also included in the display.

Figure 21:
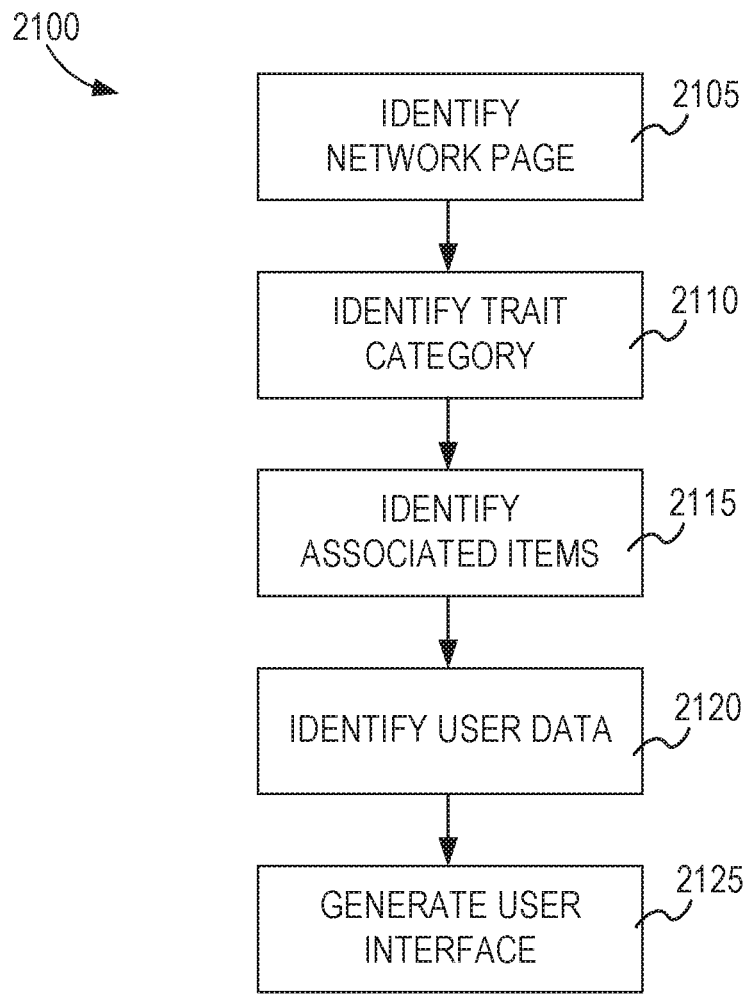
FIG. 21 shows a flow diagram of a method for managing network links and user data for inclusion in a user interface, according to some example embodiments.

FIG. 21 shows a flow diagram of a method 2100 for generating a user interface comprising network service links that are related to a user's genetic data, according to some example embodiments. At operation 2105, the trait engine 730 identifies a network page. For example, at operation 2105 the trait engine 730 identifies a newly published root page or new GWAS entry. At operation 2110, the trait engine 730 identifies a trait category (e.g., trait category 2010, trait subcategory 2010A) of a genetic variation described in the network page identified at operation 2105. At operation 2115, the trait engine 730 identifies items associated with the trait category. For example, at operation 2115, the trait engine 730 accesses trait data structure 2000 to identify an additional page that network links (e.g., hyperlinks) to the root page, and further to identify one or more network services associated with the trait category.

At operation 2120, the correlation engine 715 identifies user data in the network page identified at operation 2105. At operation 2125, the trait engine 730 generates a user interface that includes user data, network links to network services, and associated content, such as a brief description of the root page's content or additional page's content.

Figure 22:
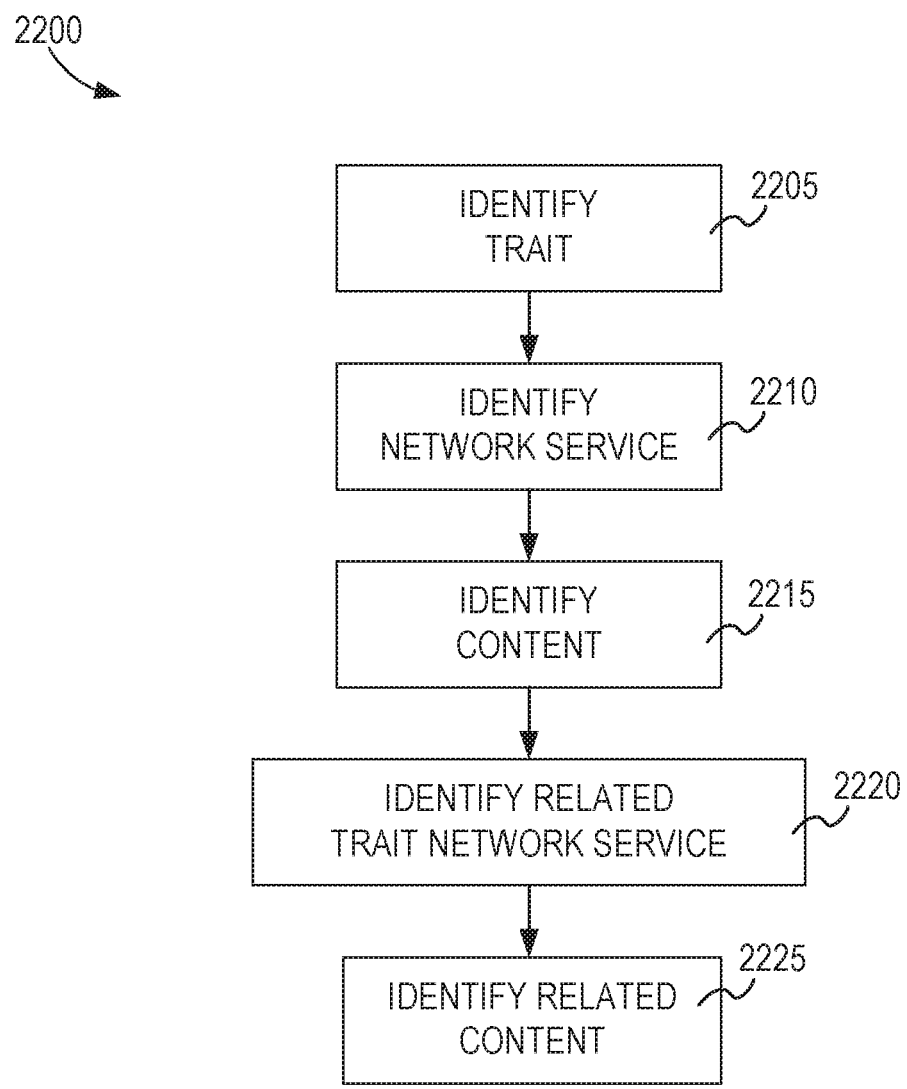
FIG. 22 shows a flow diagram of a method for identifying different network service and content items, according to some example embodiments.

FIG. 22 shows a flow diagram of a method 2200 for identifying network services related to genetic data of a user, according to some example embodiments. The operations of method 2200 can be implemented as a subroutine of operation 2115 in which items of the trait category are identified. At operation 2205, the trait engine 730 identifies a trait specified in the network page. The trait can be a specific genetic variation or expression thereof (e.g., phenotype) associated with a subcategory. For example, at operation 2205, the trait engine 730 identifies category 2010A which is related to asthma related traits. At operation 2210, the trait engine 730 identifies a network service associated with the category. For example, at operation 2210, the trait engine 730 identifies a plurality of network services 2056 associated with category 2010A. At operation 2215, the trait engine 730 identifies trait content associated with the trait category. For example, at operation 2215, the trait engine 730 identifies additional page 2054 or a summarizing description of content in the additional page 2054.

At operation 2220, the trait engine 730 identifies network services that are related to the trait. The network services can be related in that they while they do not provide analysis of the specific trait, they are in the same trait category. For example, at operation 2220, the trait engine 730 determines that subcategory 2010A is a child of category 2010 and that subcategory 2010B is a sibling trait category under category 2010. The trait engine 730 can then identify network service 2062 of subcategory 2010B as related. The identified related network service can be included in the user interface for display as relevant. At operation 2225, the trait engine 730 identifies related content. For example, at operation 2225, the trait engine 730 identifies additional page 2060 which is associated with the different trait subcategory (i.e., trait category 2010B). After operation 2225, method 2200 terminates and returns identified content to method 2100 in FIG. 21.

Figure 23A:
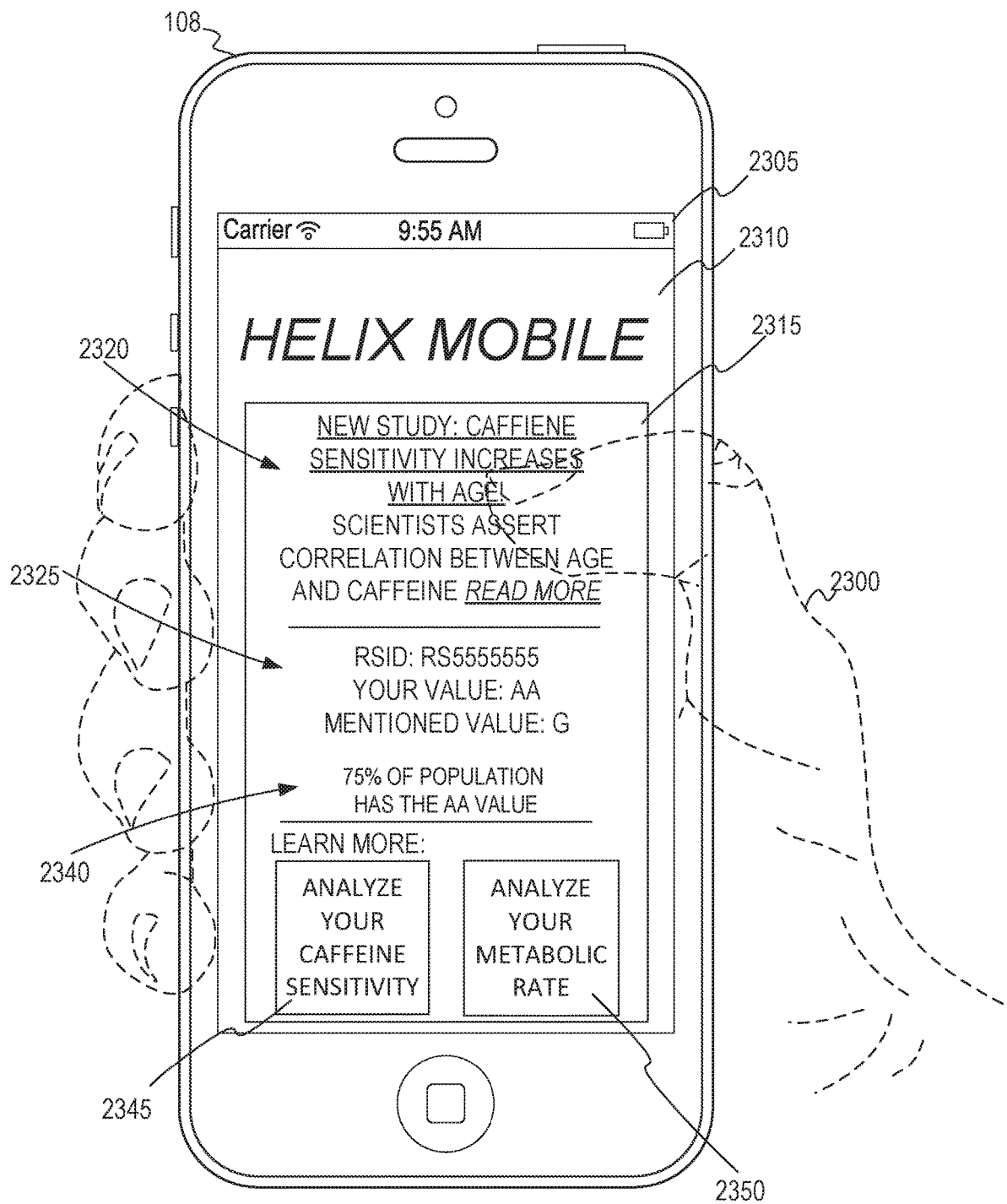
FIGS. 23A and 23B show examples of a user interface including user data and network page data, according to some example embodiments.

FIG. 23A shows an example genomic network service update user interface 2310, according to some example embodiments. As illustrated in the example of FIG. 23A, a user 2300 is holding a client device 108 having a touchscreen display 2305 currently displaying the genomic network service update user interface 2310. The genomic network service update user interface 2310 comprises a window 2315 generated in response to a root page being published on one of the pre-selected servers. The window 2315 comprises content 2320 including, for example a title and subheading with a link ("READ MORE") to an additional page linked to the root page. The window 2315 further comprises a comparison 2325 of the user's variant values to the variant values described in the root page. Further, in some example embodiments, the window 2315 includes an interpretive description 2340, which summarizes or gives context to the comparison 2325. In some embodiments, interpretive descriptions are created from the root page or additional page (e.g., extracting a sentence from the root page, or generating custom curated content from the root page or additional page) and linked to the trait category with which the root page is associated in the trait data structure 2000. In those example embodiments, when the data of comparison 2325 is displayed to a user, an interpretive description can be automatically included. The user 2300 can then gain further analysis of the data displayed in the comparison 2325 by selecting network link 2345, which directs the client device 108 to a network site of a network service associated with the trait category used to generate the window 2315. Further, a different network service is linked via network link 2350. The network service of network link 2350 is not in the same specific category (e.g., a subcategory for caffeine sensitivity) but is related through a parent category (e.g., food related genetic variations) in trait data structure 2000.

Figure 23B:
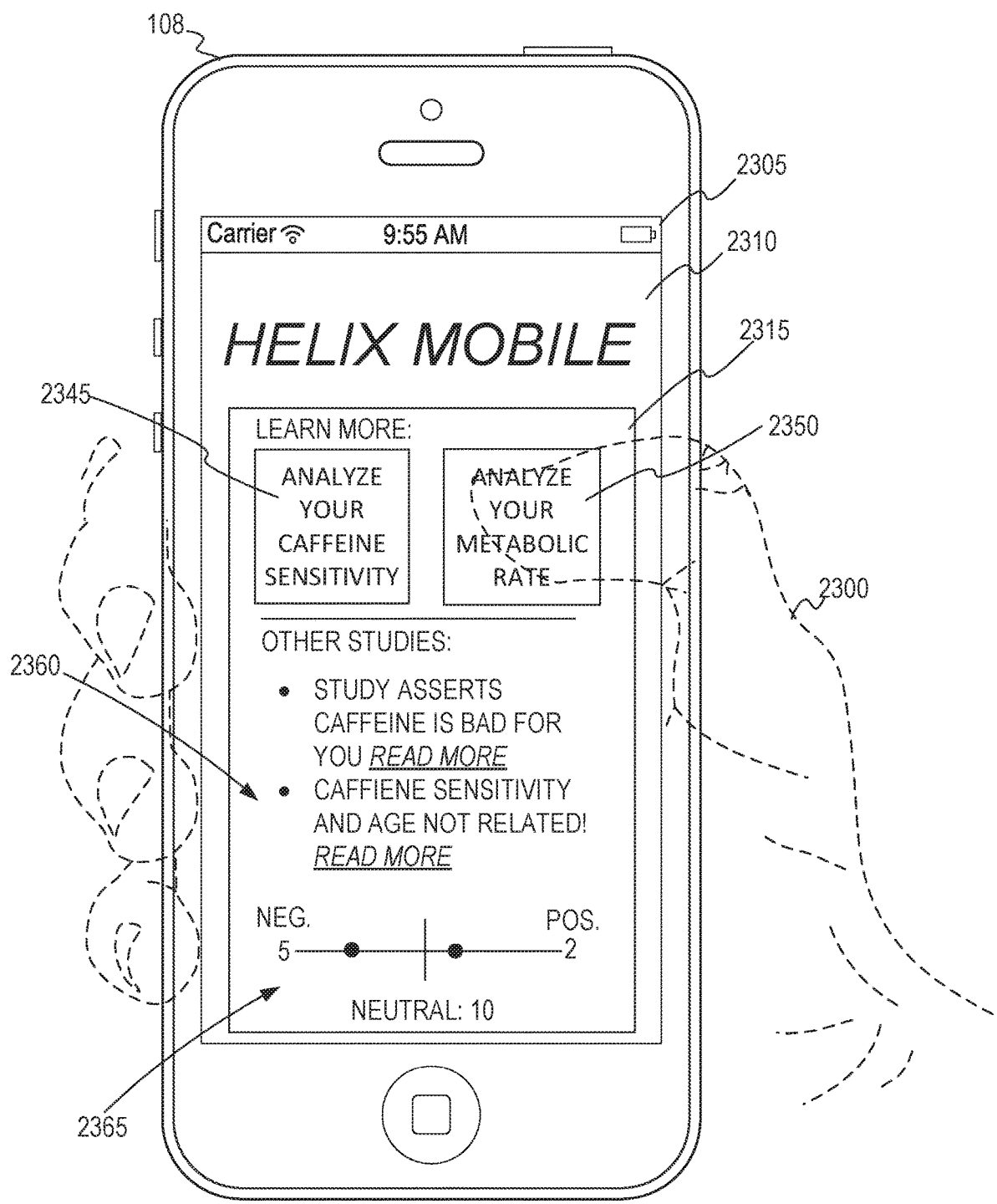

FIG. 23B shows an example genomic network service update user interface 2310, according to some example embodiments. In the example of FIG. 23B, the user 2300 has scrolled down to a lower portion of the window 2315. Below network links 2345 and 2350, existing content 2360 is displayed. The existing content 2360 can include root pages of studies or additional pages linked to the root pages that were previously published and existed in trait data structure 2000 (e.g., existing items 2080). In some embodiments, the newly published studies conflict with studies previously stored in trait data structure 2000. For example, at a first point in time a study is published that asserts red meat causes cancer, then later at a second point in time another study is published asserting that there is no relationship between red meat and cancer. As discussed above, the studies can be difficult for users (e.g., user 2300) to parse correctly through client device 108. To this end, a conflict spectrum visualization 2365 can be included in the window 2315 that gives context to potentially conflicting studies included in existing content 2360. In some embodiments, the root pages included in the trait data structure 2000 have metadata tags indicating whether they conflict with other studies. For example, the metadata tags can include a positive correlation metadata tag (e.g., a tag indicating that the root page asserts red meat causes cancer), a negative correlation metadata tag (e.g., a tag indicating that the root page asserts no relation between red meat and cancer), and a neutral metadata tag (e.g., a tag indicating inconclusive results). The conflict spectrum visualization 2365 can be auto-generated from the tags and included in the window 2315 to give visual context of newly published items.

Figure 24:
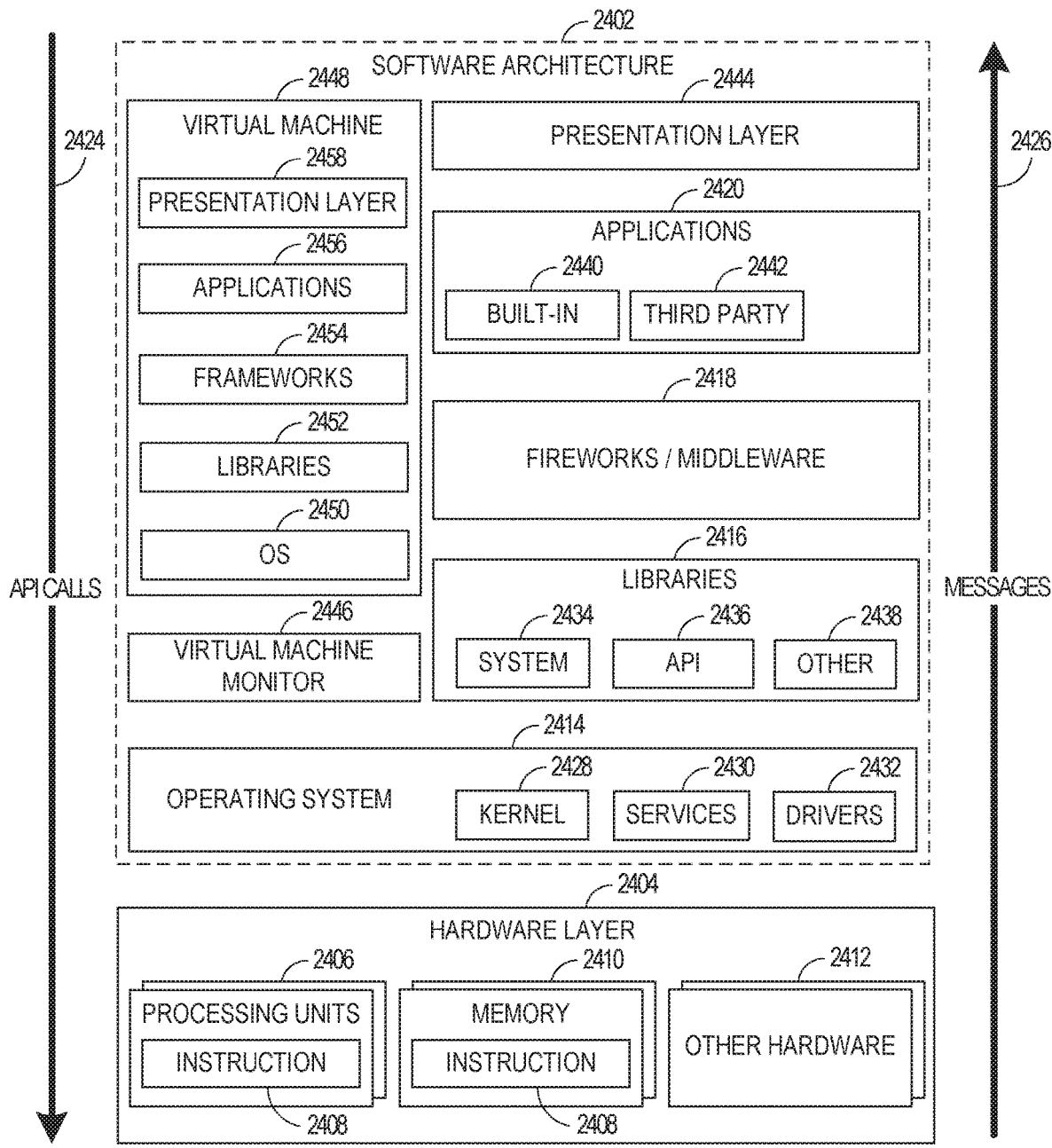
FIG. 24 is a block diagram illustrating an example of a software architecture that may be installed on a machine, according to some example embodiments.

FIG. 24 is a block diagram illustrating an example of a software architecture 2402 that may be installed on a machine, according to some example embodiments. FIG. 24 is merely a non-limiting example of a software architecture, and it will be appreciated that many other architectures may be implemented to facilitate the functionality described herein. The software architecture 2402 may be executing on hardware such as a machine 2500 of FIG. 25 that includes, among other things, processors 2510, memory 2530, and I/O components 2550. A representative hardware layer 2404 is illustrated and can represent, for example, the machine 2500 of FIG. 25. The representative hardware layer 2404 comprises one or more processing units 2406 having associated executable instructions 2408. The executable instructions 2408 represent the executable instructions of the software architecture 2402, including implementation of the methods, modules, and so forth of the above figures. The hardware layer 2404 also includes memory or storage modules 2410, which also have the executable instructions 2408. The hardware layer 2404 may also comprise other hardware 2412, which represents any other hardware of the hardware layer 2404, such as the other hardware illustrated as part of the machine 2400.

In the example architecture of FIG. 24, the software architecture 2402 may be conceptualized as a stack of layers, where each layer provides particular functionality. For example, the software architecture 2402 may include layers such as an operating system 2414, libraries 2416, frameworks/middleware 2418, applications 2420, and a presentation layer 2444. Operationally, the applications 2420 or other components within the layers may invoke API calls 2424 through the software stack and receive a response, returned values, and so forth (illustrated as messages 2426) in response to the API calls 2424. The layers illustrated are representative in nature, and not all software architectures have all layers. For example, some mobile or special purpose operating systems may not provide a frameworks/middleware 2418 layer, while others may provide such a layer. Other software architectures may include additional or different layers.

The operating system 2414 may manage hardware resources and provide common services. The operating system 2414 may include, for example, a kernel 2428, services 2430, and drivers 2432. The kernel 2428 may act as an abstraction layer between the hardware and the other software layers. For example, the kernel 2428 may be responsible for memory management, processor management (e.g., scheduling), component management, networking, security settings, and so on. The services 2430 may provide other common services for the other software layers. The drivers 2432 may be responsible for controlling or interfacing with the underlying hardware. For instance, the drivers 2432 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 2416 may provide a common infrastructure that may be utilized by the applications 2420 and/or other components and/or layers. The libraries 2416 typically provide functionality that allows other software modules to perform tasks in an easier fashion than by interfacing directly with the underlying operating system 2414 functionality (e.g., kernel 2428, services 2430, or drivers 2432). The libraries 2416 may include system libraries 2434 (e.g., C standard library) that may provide functions such as memory allocation functions, string manipulation functions, mathematic functions, and the like. In addition, the libraries 2416 may include API libraries 2436 such as media libraries (e.g., libraries to support presentation and manipulation of various media formats such as MPEG4, H.264, MP3, AAC, AMR, JPG, PNG), graphics libraries (e.g., an OpenGL framework that may be used to render 2D and 3D graphic content on a display), database libraries (e.g., SQLite that may provide various relational database functions), web libraries (e.g., WebKit that may provide web browsing functionality), and the like. The libraries 2416 may also include a wide variety of other libraries 2438 to provide many other APIs to the applications 2420 and other software components/modules.

The frameworks 2418 (also sometimes referred to as middleware) may provide a higher-level common infrastructure that may be utilized by the applications 2420 or other software components/modules. For example, the frameworks 2418 may provide various graphic user interface (GUI) functions, high-level resource management, high-level location services, and so forth. The frameworks 2418 may provide a broad spectrum of other APIs that may be utilized by the applications 2420 and/or other software components/modules, some of which may be specific to a particular operating system or platform.

The applications 2420 include built-in applications 2440 and/or third-party applications 2442. Examples of representative built-in applications 2440 may include, but are not limited to, a home application, a contacts application, a browser application, a book reader application, a location application, a media application, a messaging application, or a game application.

The third-party applications 2442 may include any of the built-in applications 2440, as well as a broad assortment of other applications. In a specific example, the third-party applications 2442 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third-party applications 2442 may invoke the API calls 2424 provided by the mobile operating system such as the operating system 2414 to facilitate functionality described herein.

The applications 2420 may utilize built-in operating system functions (e.g., kernel 2428, services 2430, or drivers 2432), libraries (e.g., system libraries 2434, API libraries 2436, and other libraries 2438), or frameworks/middleware 2418 to create user interfaces to interact with users of the system. Alternatively, or additionally, in some systems, interactions with a user may occur through a presentation layer, such as the presentation layer 2444. In these systems, the application/module "logic" can be separated from the aspects of the application/module that interact with the user.

Some software architectures utilize virtual machines. In the example of FIG. 24, this is illustrated by a virtual machine 2448. A virtual machine creates a software environment where applications/modules can execute as if they were executing on a hardware machine e.g., the machine 2500 of FIG. 25, for example). A virtual machine 2448 is hosted by a host operating system (e.g., operating system 2414) and typically, although not always, has a virtual machine monitor 2446, which manages the operation of the virtual machine 2448 as well as the interface with the host operating system (e.g., operating system 2414). A software architecture executes within the virtual machine 2448, such as an operating system 2450, libraries 2452, frameworks/middleware 2454, applications 2456, or a presentation layer 2458. These layers of software architecture executing within the virtual machine 2448 can be the same as corresponding layers previously described or may be different.

Figure 25:
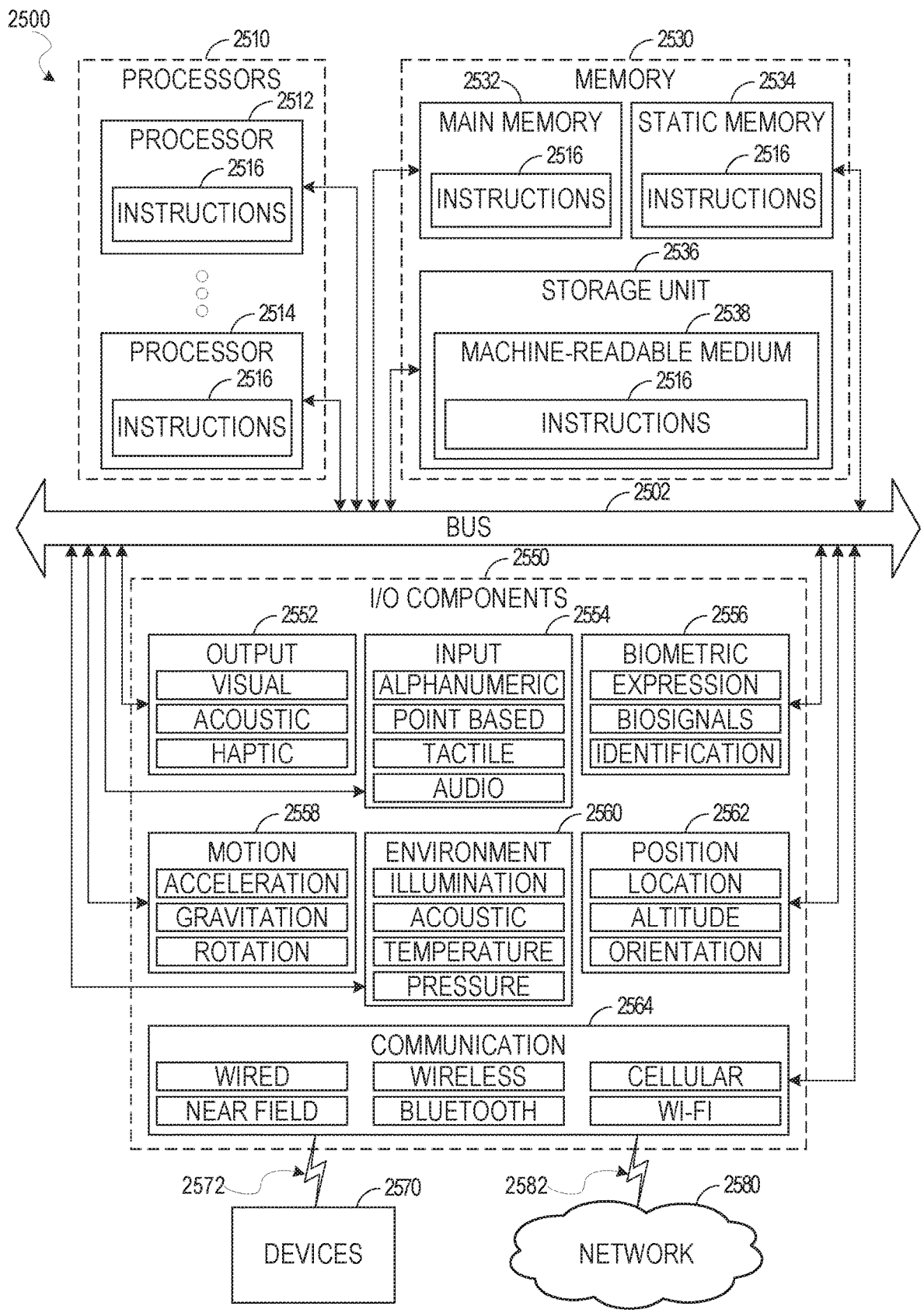
FIG. 25 illustrates a diagrammatic representation of a machine in the form of a computer system within which a set of instructions may be executed for causing the machine to perform any one or more of the methodologies discussed herein, according to an example embodiment.

FIG. 25 illustrates a diagrammatic representation of a machine 2500 in the form of a computer system within which a set of instructions may be executed for causing the machine to perform any one or more of the methodologies discussed herein, according to an example embodiment. Specifically, FIG. 25 shows a diagrammatic representation of the machine 2500 in the example form of a computer system, within which instructions 2516 (e.g., software, a program, an application, an applet, an app, or other executable code) for causing the machine 2500 to perform any one or more of the methodologies discussed herein may be executed. For example, the instructions 2516 may cause the machine 2500 to execute the methods of FIGS. 9-14. The instructions 2516 transform the general, non-programmed machine 2500 into a particular machine 2500 programmed to carry out the described and illustrated functions in the manner described. In alternative embodiments, the machine 2500 operates as a standalone device or may be coupled (e.g., networked) to other machines. In a networked deployment, the machine 2500 may operate in the capacity of a server machine or a client machine in a server-client network environment, or as a peer machine in a peer-to-peer (or distributed) network environment. The machine 2500 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network root, a network switch, a network bridge, or any machine capable of executing the instructions 2516, sequentially or otherwise, that specify actions to be taken by the machine 2500. Further, while only a single machine 2500 is illustrated, the term "machine" shall also be taken to include a collection of machines 2500 that individually or jointly execute the instructions 2516 to perform any one or more of the methodologies discussed herein.

The machine 2500 may include processors 2510, memory 2530, and I/O components 2550, which may be configured to communicate with each other such as via a bus 2502. In an example embodiment, the processors 2510 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 2512 and a processor 2514 that may execute the instructions 2516. The term "processor" is intended to include multi-core processors that may comprise two or more independent processors (sometimes referred to as "cores") that may execute instructions contemporaneously. Although FIG. 25 shows multiple processors 2510, the machine 2500 may include a single processor with a single core, a single processor with multiple cores (e.g., a multi-core processor), multiple processors with a single core, multiple processors with multiples cores, or any combination thereof.

The memory 2530 may include a main memory 2532, a static memory 2534, and a storage unit 2536, both accessible to the processors 2510 such as via the bus 2502. The main memory 2530, the static memory 2534, and storage unit 2536 store the instructions 2516 embodying any one or more of the methodologies or functions described herein. The instructions 2516 may also reside, completely or partially, within the main memory 2532, within the static memory 2534, within the storage unit 2536, within at least one of the processors 2510 (e.g., within the processor's cache memory), or any suitable combination thereof, during execution thereof by the machine 2500.

The I/O components 2550 may include a wide variety of components to receive input, provide output, produce output, transmit information, exchange information, capture measurements, and so on. The specific I/O components 2550 that are included in a particular machine will depend on the type of machine. For example, portable machines such as mobile phones will likely include a touch input device or other such input mechanisms, while a headless server machine will likely not include such a touch input device. It will be appreciated that the I/O components 2550 may include many other components that are not shown in FIG. 25. The I/O components 2550 are grouped according to functionality merely for simplifying the following discussion and the grouping is in no way limiting. In various example embodiments, the I/O components 2550 may include output components 2552 and input components 2554. The output components 2552 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 2554 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 2550 may include biometric components 2556, motion components 2558, environmental components 2560, or position components 2562, among a wide array of other components. For example, the biometric components 2556 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 2558 may include acceleration sensor components (e.g., accelerometer), gravitation sensor components, rotation sensor components (e.g., gyroscope), and so forth. The environmental components 2560 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 2562 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 2550 may include communication components 2564 operable to couple the machine 2500 to a network 2580 or devices 2570 via a coupling 2582 and a coupling 2572, respectively. For example, the communication components 2564 may include a network interface component or another suitable device to interface with the network 2580. In further examples, the communication components 2564 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 2570 may be another machine or any of a wide variety of peripheral devices (e.g., a peripheral device coupled via a USB).

Moreover, the communication components 2564 may detect identifiers or include components operable to detect identifiers. For example, the communication components 2564 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 2564, such as location via Internet Protocol (IP) geolocation, location via Wi-Fi® signal triangulation, location via detecting an NFC beacon signal that may indicate a particular location, and so forth.

Executable Instructions and Machine Storage Medium

The various memories (i.e., 2530, 2532, 2534, and/or memory of the processor(s) 2510) and/or storage unit 2536 may store one or more sets of instructions and data structures (e.g., software) embodying or utilized by any one or more of the methodologies or functions described herein. These instructions (e.g., the instructions 2516), when executed by processor(s) 2510, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

Transmission Medium

In various example embodiments, one or more portions of the network 2580 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 2580 or a portion of the network 2580 may include a wireless or cellular network, and the coupling 2582 may be a Code Division Multiple Access (CDMA) connection, a Global System for Mobile communications (GSM) connection, or another type of cellular or wireless coupling. In this example, the coupling 2582 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 2516 may be transmitted or received over the network 2580 using a transmission medium via a network interface device (e.g., a network interface component included in the communication components 2564) and utilizing any one of a number of well-known transfer protocols (e.g., hypertext transfer protocol (HTTP)). Similarly, the instructions 2516 may be transmitted or received using a transmission medium via the coupling 2572 (e.g., a peer-to-peer coupling) to the devices 2570. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 2516 for execution by the machine 2500, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

Computer-Readable Medium

The terms "machine-readable medium," "computer-readable medium" and "device-readable medium" mean the same thing and may be used interchangeably in this disclosure. The terms are defined to include both machine-storage media and transmission media. Thus, the terms include both storage devices/media and carrier waves/modulated data signals.

What is claimed is:

1. A method comprising:

receiving a plurality of network pages from one or more select network servers, each network page having alleles of a genetic variation that is uniquely identified on the one or more select network servers by a genetic variation identifier;

accessing user allele values in a genetic variation structured data file of a user, the genetic variation structured data file having access ranges to sequence data of the user, wherein an access server manages access by a plurality of external network services to the access ranges of the sequence data of the user, the access server having user access settings to configure pre-authorized access to individual ranges of the sequence data by one or more of the plurality of external network services;

receiving, from a first network service of the plurality of external network services, a request for access to a first portion of the user allele values in the genetic variation structured data file that matches a first set of alleles in a first network page from the plurality of network pages, the first network service having pre-authorized access, by the access server, to a first access range that includes the first portion of the user allele values;

receiving, from a second network service of the plurality of external network services, a request for access to a second portion of the user allele values that match a second set of alleles in a second network page from the plurality of network pages, the second network service having pre-authorized access, by the access server, to a second access range that includes the second portion of the user allele values;

identifying a first additional network page that links to the first network page from the plurality of select network servers;

identifying a second additional network page that links to the second network page from the plurality of select network servers;

generating a user interface displaying data from the first additional network page and the second additional network page based at least in part on the first additional network page linking to the first network page and the second additional network page linking to the second network page, and further based on the first network service having pre-authorized access to the first portion of the user allele values and the second network service having pre-authorized access to the second portion of the user allele values; and causing, on a client device of the user, presentation of the user interface.

2. The method of claim 1, further comprising:
identifying links to the plurality of network pages in a database storing genetic genome structured data.

3. The method of claim 2, further comprising: filtering one or more pages not hosted on the one or more select network servers.

4. The method of claim 2, wherein the database storing genome structured data includes pages from a plurality of network servers, and the method further comprises:
receiving selections of one or more of the plurality of network servers;
storing the selections as the one or more select network servers.

5. The method of claim 2, further comprising:
receiving an update to the database; and
responsive to the update, updating the user interface to include content of a page linked to a network page in the update to the database based on the network page having alleles that match another portion of the user allele values.

6. The method of claim 1, wherein the first additional network page is not from the one or more select network servers, and wherein the second additional network page is not from the one or more select network servers.

7. The method of claim 1, wherein the user interface includes a genetic variation category selection element that is operable to include or exclude display of content of the first additional network page.

8. The method of claim 1, further comprising:
determining that another portion of the user allele values in the genetic variation structured data file does not match any of the alleles in one or more of the plurality of network pages.

9. The method of claim 8, wherein the user interface does not include content from the plurality of network pages that have alleles that do not match the user allele values.

10. The method of claim 1, further comprising:
identifying network links in the plurality of network pages that link to a plurality of additional network pages that include the first additional network page and the second additional network page; and
storing the data from the first additional network page and the second additional network page for display in the user interface.

11. The method of claim 10, wherein the data from the additional network pages includes user interface content configured for display in the additional networked pages.

12. The method of claim 11, wherein the user interface content of the additional networked pages includes one or more of: text data, image data, video data.

13. The method of claim 1, wherein the genetic variation identifier is a reference single nucleotide polymorphism identifier (RSID).

14. The method of claim 1, wherein the genetic variation structured data file is a variant call format (VCF) file.

15. A system comprising:
one or more processors of a client device; and
a memory storing instructions that, when executed by the one or more processors, cause the system to perform operations comprising:
receiving a plurality of network pages from one or more select network servers, each network page having alleles of a genetic variation that is uniquely identified on the one or more select network servers by a genetic variation identifier;
accessing user allele values in a genetic variation structured data file of a user, the genetic variation structured data file having access ranges to sequence data of the user, wherein an access server manages access by a plurality of external network services to the access ranges of the sequence data of the user, the access server having user access settings to configure pre-authorized access to individual ranges of the sequence data by one or more of the plurality of external network services;
receiving, from a first network service of the plurality of external network services, a request for access to a first portion of the user allele values in the genetic variation structured data file that matches a first set of alleles in a first network page from the plurality of network pages, the first network service having pre-authorized access, by the access server, to a first access range that includes the first portion of the user allele values;
receiving, from a second network service of the plurality of external network services, a request for access to a second portion of the user allele values that match a second set of alleles in a second network page from the plurality of network pages, the second network service having pre-authorized access, by the access server, to a second access range that includes the second portion of the user allele values;
identifying a first additional network page that links to the first network page from the plurality of select network servers;
identifying a second additional network page that links to the second network page from the plurality of select network servers;
generating a user interface displaying data from the first additional network page and the second additional network page based at least in part on the first additional network page linking to the first network page and the second additional network page linking to the second network page, and further based on the first network service having pre-authorized access to the first portion of the user allele values and the second network service having pre-authorized access to the second portion of the user allele values; and
causing, on a client device of the user, presentation of the user interface.

16. A machine-readable storage device embodying instructions that, when executed by a device, cause the device to perform operations comprising:
receiving a plurality of network pages from one or more select network servers, each network page having alleles of a genetic variation that is uniquely identified on the one or more select network servers by a genetic variation identifier;

accessing user allele values in a genetic variation structured data file of a user, the genetic variation structured data file having access ranges to sequence data of the user, wherein an access server manages access by a plurality of external network services to the access ranges of the sequence data of the user, the access server having user access settings to configure pre-authorized access to individual ranges of the sequence data by one or more of the plurality of external network services;

receiving, from a first network service of the plurality of external network services, a request for access to a first portion of the user allele values in the genetic variation structured data file that matches a first set of alleles in a first network page from the plurality of network pages, the first network service having pre-authorized access, by the access server, to a first access range that includes the first portion of the user allele values;

receiving, from a second network service of the plurality of external network services, a request for access to a second portion of the user allele values that match a second set of alleles in a second network page from the plurality of network pages, the second network service having pre-authorized access, by the access server, to a second access range that includes the second portion of the user allele values;

identifying a first additional network page that links to the first network page from the plurality of select network servers;

identifying a second additional network page that links to the second network page from the plurality of select network servers;

generating a user interface displaying data from the first additional network page and the second additional network page based at least in part on the first additional network page linking to the first network page and the second additional network page linking to the second network page, and further based on the first network service having pre-authorized access to the first portion of the user allele values and the second network service having pre-authorized access to the second portion of the user allele values; and causing, on a client device of the user, presentation of the user interface.

* * * * *

UNITED STATES PATENT AND TRADEMARK OFFICE
CERTIFICATE OF CORRECTION

Page 1 of 1

PATENT NO. : 10,861,587 B2
APPLICATION NO. : 16/169822
DATED : December 8, 2020
INVENTOR(S) : Dunaway et al.

It is certified that error appears in the above-identified patent and that said Letters Patent is hereby corrected as shown below:

In the Specification

In Column 6, Line 6, delete "DNA." and insert --DNA,-- therefor

In Column 7, Line 59, delete "308" and insert --306-- therefor

In Column 13, Line 52, delete "age" and insert --page-- therefor

In Column 15, Line 21, delete "provider" and insert --partner-- therefor

In Column 26, Line 27, before "e.g.,", insert --(--

In the Claims

In Column 31, Line 22, in Claim 2, after "storing", delete "genetic"

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*